US012465515B2

(12) United States Patent
Brooks

(10) Patent No.: US 12,465,515 B2
(45) Date of Patent: Nov. 11, 2025

(54) FLUID COLLECTION ASSEMBLIES INCLUDING A SAMPLE PORT

(71) Applicant: PUREWICK CORPORATION, El Cajon, CA (US)

(72) Inventor: Christopher K. Brooks, Decatur, GA (US)

(73) Assignee: PUREWICK CORPORATION, Covington, GA (US)

( * ) Notice: Subject to any disclaimer, the term of this patent is extended or adjusted under 35 U.S.C. 154(b) by 863 days.

(21) Appl. No.: 17/755,236

(22) PCT Filed: Oct. 27, 2020

(86) PCT No.: PCT/US2020/057562
§ 371 (c)(1),
(2) Date: Apr. 25, 2022

(87) PCT Pub. No.: WO2021/086868
PCT Pub. Date: May 6, 2021

(65) Prior Publication Data

US 2022/0395390 A1 Dec. 15, 2022

Related U.S. Application Data

(60) Provisional application No. 62/926,767, filed on Oct. 28, 2019.

(51) Int. Cl.

| | |
|---|---|
| ***A61F 5/451*** | (2006.01) |
| ***A61B 10/00*** | (2006.01) |
| ***A61F 5/44*** | (2006.01) |

(52) U.S. Cl.
CPC ............ *A61F 5/451* (2013.01); *A61B 10/007* (2013.01); *A61F 5/4401* (2013.01); *A61F 5/4405* (2013.01)

(58) Field of Classification Search
CPC .......... A61F 5/451; A61F 5/44; A61F 5/4405; A61F 5/4401; A61F 5/453; A61B 10/007; A61B 10/0045
(Continued)

(56) References Cited

U.S. PATENT DOCUMENTS

| | | |
|---|---|---|
| 737,443 A | 8/1903 | Mooers |
| 1,015,905 A | 1/1912 | Northrop |

(Continued)

FOREIGN PATENT DOCUMENTS

| | | |
|---|---|---|
| AU | 2018216821 A1 | 8/2019 |
| AU | 2021299304 A1 | 2/2023 |

(Continued)

OTHER PUBLICATIONS

US 9,908,683 B2, 03/2018, Sandhausen et al. (withdrawn)

(Continued)

*Primary Examiner* — Rafael A Ortiz

(57) ABSTRACT

Fluid collection assemblies (100, 200, 300*a*, 300*b*, 400*a*, 400*b*, 500, 600) including a sample port (112, 212, 312, 412*a*, 412*b*, 512), systems (146*a*) including the same, and methods of using the same are disclosed herein. An example fluid collection assembly (100) includes a fluid impermeable barrier (102) including a first end region (104), a second end region (106) opposite the first end region, and a sump (108) that forms at least a portion of the first end region. The fluid impermeable barrier also defines at least one opening (114) between the first end region and the second end region and a fluid reservoir that is defined by at least a portion of the sump. The fluid collection assembly also includes at least one wicking material (138) disposed in the chamber (116) and a sample port (112) extending from the sump. The sample port is configured to be connected to a fluid collector (144*a*). The sample port is in fluid communication with the (Continued)

fluid reservoir (110) such that a sample of the bodily fluids received by the fluid collection assembly may be obtained.

22 Claims, 8 Drawing Sheets

(58) Field of Classification Search
USPC .......................................................... 220/694
See application file for complete search history.

(56) References Cited

U.S. PATENT DOCUMENTS

| | | | |
|---|---|---|---|
| 1,032,841 | A | 7/1912 | Koenig |
| 1,178,644 | A | 4/1916 | Johnson |
| 1,387,726 | A | 8/1921 | Karge |
| 1,742,080 | A | 12/1929 | Jones |
| 1,979,899 | A | 11/1934 | Obrien et al. |
| 2,241,010 | A | 5/1941 | Chipley |
| 2,262,772 | A | 11/1941 | Peder |
| 2,326,881 | A | 8/1943 | Packer |
| 2,379,346 | A | 6/1945 | Farrell |
| 2,485,555 | A | 10/1949 | Bester |
| 2,571,357 | A | 10/1951 | Charles |
| 2,613,670 | A | 10/1952 | Edward |
| 2,616,426 | A | 11/1952 | Adele |
| 2,644,234 | A | 7/1953 | Earl |
| 2,648,335 | A | 8/1953 | Chambers |
| 2,859,786 | A | 11/1958 | Tupper |
| 2,944,551 | A | 7/1960 | Carl |
| 2,968,046 | A | 1/1961 | Duke |
| 2,971,512 | A | 2/1961 | Reinhardt |
| 3,032,038 | A | 5/1962 | Swinn |
| 3,077,883 | A | 2/1963 | Hill |
| 3,087,938 | A | 4/1963 | Hans et al. |
| 3,114,916 | A | 12/1963 | Hadley |
| 3,169,528 | A | 2/1965 | Knox et al. |
| 3,171,506 | A | 3/1965 | Therkel |
| 3,175,719 | A | 3/1965 | Herndon |
| 3,194,238 | A | 7/1965 | Breece |
| 3,198,994 | A | 8/1965 | Hildebrandt et al. |
| 3,221,742 | A | 12/1965 | Egon |
| 3,312,221 | A | 4/1967 | Overment |
| 3,312,981 | A | 4/1967 | McGuire et al. |
| 3,349,768 | A | 10/1967 | Keane |
| 3,362,590 | A | 1/1968 | Gene |
| 3,366,116 | A | 1/1968 | Huck |
| 3,398,848 | A | 8/1968 | Donovan |
| 3,400,717 | A | 9/1968 | Bruce et al. |
| 3,406,688 | A | 10/1968 | Bruce |
| 3,424,163 | A | 1/1969 | Gravdahl |
| 3,425,471 | A | 2/1969 | Yates |
| 3,434,565 | A | 3/1969 | Fischer |
| 3,511,241 | A | 5/1970 | Lee |
| 3,512,185 | A | 5/1970 | Ellis |
| 3,520,300 | A | 7/1970 | Flower |
| 3,528,423 | A | 9/1970 | Lee |
| 3,608,552 | A | 9/1971 | Broerman |
| 3,613,123 | A | 10/1971 | Langstrom |
| 3,648,700 | A | 3/1972 | Warner |
| 3,651,810 | A | 3/1972 | Ormerod |
| 3,661,155 | A | 5/1972 | Lindan |
| 3,683,918 | A | 8/1972 | Pizzella |
| 3,699,815 | A | 10/1972 | Holbrook |
| 3,726,277 | A | 4/1973 | Hirschman |
| 3,742,952 | A | 7/1973 | Magers et al. |
| 3,757,355 | A | 9/1973 | Allen et al. |
| 3,788,324 | A | 1/1974 | Lim |
| 3,843,016 | A | 10/1974 | Bornhorst et al. |
| 3,863,638 | A | 2/1975 | Rogers et al. |
| 3,863,798 | A | 2/1975 | Kurihara et al. |
| 3,864,759 | A | 2/1975 | Horiuchi |
| 3,865,109 | A | 2/1975 | Elmore et al. |
| 3,881,486 | A | 5/1975 | Fenton |
| 3,881,489 | A | 5/1975 | Hartwell |
| 3,915,189 | A | 10/1975 | Holbrook et al. |
| 3,931,650 | A | 1/1976 | Miller |
| 3,998,228 | A | 12/1976 | Poidomani |
| 3,999,550 | A | 12/1976 | Martin |
| 4,006,793 | A | 2/1977 | Robinson |
| 4,015,604 | A | 4/1977 | Csillag |
| 4,020,843 | A | 5/1977 | Kanall |
| 4,022,213 | A | 5/1977 | Stein |
| 4,027,776 | A | 6/1977 | Douglas |
| 4,031,897 | A | 6/1977 | Graetz |
| 4,064,962 | A | 12/1977 | Hunt |
| 4,069,817 | A | 1/1978 | Fenole et al. |
| 4,084,589 | A | 4/1978 | Kulvi |
| 4,096,897 | A | 6/1978 | Cammarata |
| 4,116,197 | A | 9/1978 | Bermingham |
| 4,180,178 | A | 12/1979 | Turner |
| 4,187,953 | A | 2/1980 | Turner |
| 4,194,508 | A | 3/1980 | Anderson |
| 4,200,102 | A | 4/1980 | Duhamel et al. |
| 4,202,058 | A | 5/1980 | Anderson |
| 4,203,503 | A | 5/1980 | Bertotti et al. |
| 4,209,076 | A | 6/1980 | Bertotti et al. |
| 4,223,677 | A | 9/1980 | Anderson |
| 4,233,025 | A | 11/1980 | Larson et al. |
| 4,233,978 | A | 11/1980 | Hickey |
| 4,246,901 | A | 1/1981 | Frosch et al. |
| 4,253,542 | A | 3/1981 | Ruspa et al. |
| 4,257,418 | A | 3/1981 | Hessner |
| 4,270,539 | A | 6/1981 | Frosch et al. |
| 4,280,498 | A | 7/1981 | Jensen |
| 4,281,655 | A | 8/1981 | Terauchi |
| 4,292,916 | A | 10/1981 | Bradley et al. |
| 4,330,239 | A | 5/1982 | Gannaway |
| 4,345,341 | A | 8/1982 | Saito |
| 4,349,029 | A | 9/1982 | Mott |
| 4,352,356 | A | 10/1982 | Tong |
| 4,360,933 | A | 11/1982 | Kimura et al. |
| 4,365,363 | A | 12/1982 | Windauer |
| 4,375,841 | A | 3/1983 | Vielbig |
| 4,387,726 | A | 6/1983 | Denard |
| 4,403,991 | A | 9/1983 | Hill |
| 4,421,511 | A | 12/1983 | Steer et al. |
| 4,425,130 | A | 1/1984 | Desmarais |
| 4,446,986 | A | 5/1984 | Bowen et al. |
| 4,453,938 | A | 6/1984 | Brendling |
| 4,457,314 | A | 7/1984 | Knowles |
| 4,476,879 | A | 10/1984 | Jackson |
| 4,526,688 | A | 7/1985 | Schmidt et al. |
| 4,528,703 | A | 7/1985 | Kraus |
| 4,533,354 | A | 8/1985 | Jensen et al. |
| 4,533,357 | A | 8/1985 | Hall |
| D280,438 | S | 9/1985 | Wendt |
| 4,551,141 | A | 11/1985 | Mcneil |
| 4,553,968 | A | 11/1985 | Komis |
| 4,568,341 | A | 2/1986 | Mitchell et al. |
| 4,581,026 | A | 4/1986 | Schneider |
| 4,583,983 | A | 4/1986 | Einhorn et al. |
| 4,589,516 | A | 5/1986 | Inoue et al. |
| 4,601,716 | A | 7/1986 | Smith |
| 4,610,675 | A | 9/1986 | Triunfol |
| 4,620,333 | A | 11/1986 | Ritter |
| 4,626,250 | A | 12/1986 | Schneider |
| 4,627,846 | A | 12/1986 | Ternstroem |
| 4,631,061 | A | 12/1986 | Martin |
| 4,650,477 | A | 3/1987 | Johnson |
| 4,655,754 | A | 4/1987 | Richmond et al. |
| 4,656,675 | A | 4/1987 | Fajnsztajn |
| 4,681,570 | A | 7/1987 | Dalton |
| 4,681,572 | A | 7/1987 | Tokarz et al. |
| 4,681,577 | A | 7/1987 | Stern et al. |
| 4,692,160 | A | 9/1987 | Nussbaumer |
| 4,707,864 | A | 11/1987 | Ikematsu et al. |
| 4,713,065 | A | 12/1987 | Koot |
| 4,713,066 | A | 12/1987 | Komis |
| 4,723,953 | A | 2/1988 | Pratt et al. |
| 4,735,841 | A | 4/1988 | Sourdet |
| 4,743,236 | A | 5/1988 | Manschot |
| 4,747,166 | A | 5/1988 | Kuntz |
| 4,752,944 | A | 6/1988 | Conrads et al. |
| 4,769,215 | A | 9/1988 | Ehrenkranz |

(56) References Cited

U.S. PATENT DOCUMENTS

| | | | |
|---|---|---|---|
| 4,771,484 | A | 9/1988 | Mozell |
| 4,772,280 | A | 9/1988 | Rooyakkers |
| 4,784,654 | A | 11/1988 | Beecher |
| 4,790,830 | A | 12/1988 | Hamacher |
| 4,790,835 | A | 12/1988 | Elias |
| 4,791,686 | A | 12/1988 | Taniguchi et al. |
| 4,795,449 | A | 1/1989 | Schneider et al. |
| 4,798,603 | A | 1/1989 | Meyer et al. |
| 4,799,928 | A | 1/1989 | Crowley |
| 4,804,377 | A | 2/1989 | Hanifl et al. |
| 4,812,053 | A | 3/1989 | Bhattacharjee |
| 4,813,943 | A | 3/1989 | Smith |
| 4,820,291 | A | 4/1989 | Terauchi et al. |
| 4,820,297 | A | 4/1989 | Kaufman et al. |
| 4,841,728 | A | 6/1989 | Jean et al. |
| 4,846,818 | A | 7/1989 | Keldahl et al. |
| 4,846,819 | A | 7/1989 | Welch |
| 4,846,824 | A | 7/1989 | Schultz et al. |
| 4,846,909 | A | 7/1989 | Klug et al. |
| 4,865,595 | A | 9/1989 | Heyden |
| 4,880,417 | A | 11/1989 | Yabrov et al. |
| 4,882,794 | A | 11/1989 | Stewart |
| 4,883,465 | A | 11/1989 | Brennan |
| 4,886,498 | A | 12/1989 | Newton |
| 4,886,508 | A | 12/1989 | Washington |
| 4,886,509 | A | 12/1989 | Mattsson |
| 4,889,532 | A | 12/1989 | Metz et al. |
| 4,889,533 | A | 12/1989 | Beecher |
| 4,890,691 | A | 1/1990 | Ching-Ho |
| 4,895,140 | A | 1/1990 | Bellak |
| 4,903,254 | A | 2/1990 | Haas |
| 4,904,248 | A | 2/1990 | Vaillancourt |
| 4,905,692 | A | 3/1990 | More |
| 4,911,262 | A | 3/1990 | Tani et al. |
| 4,930,997 | A | 6/1990 | Bennett |
| 4,936,838 | A | 6/1990 | Cross et al. |
| 4,950,262 | A | 8/1990 | Takagi |
| 4,955,922 | A | 9/1990 | Terauchi |
| 4,957,487 | A | 9/1990 | Gerow |
| 4,965,460 | A | 10/1990 | Tanaka et al. |
| 4,986,823 | A | 1/1991 | Anderson et al. |
| 4,987,849 | A | 1/1991 | Sherman |
| 5,002,541 | A | 3/1991 | Conkling et al. |
| 5,004,463 | A | 4/1991 | Nigay |
| 5,013,308 | A | 5/1991 | Sullivan et al. |
| 5,031,248 | A | 7/1991 | Kemper |
| 5,045,077 | A | 9/1991 | Blake |
| 5,045,283 | A | 9/1991 | Patel |
| 5,049,144 | A | 9/1991 | Payton |
| 5,053,339 | A | 10/1991 | Patel |
| 5,057,092 | A | 10/1991 | Webster |
| 5,058,088 | A | 10/1991 | Haas et al. |
| 5,071,347 | A | 12/1991 | McGuire |
| 5,078,707 | A | 1/1992 | Peter |
| 5,084,037 | A | 1/1992 | Barnett |
| 5,100,396 | A | 3/1992 | Zamierowski |
| 5,102,404 | A | 4/1992 | Goldberg et al. |
| 5,112,324 | A | 5/1992 | Wallace |
| 5,137,033 | A | 8/1992 | Norton |
| 5,147,301 | A | 9/1992 | Ruvio |
| 5,176,667 | A | 1/1993 | Debring |
| 5,195,997 | A | 3/1993 | Carns |
| 5,196,654 | A | 3/1993 | Diflora et al. |
| 5,199,444 | A | 4/1993 | Wheeler |
| 5,203,699 | A | 4/1993 | McGuire |
| 5,244,458 | A | 9/1993 | Takasu |
| 5,246,454 | A | 9/1993 | Peterson |
| 5,267,988 | A | 12/1993 | Farkas |
| 5,275,307 | A | 1/1994 | Freese |
| 5,282,795 | A | 2/1994 | Finney |
| 5,294,983 | A | 3/1994 | Ersoz et al. |
| 5,295,979 | A | 3/1994 | Delaurentis et al. |
| 5,295,983 | A | 3/1994 | Kubo |
| 5,300,052 | A * | 4/1994 | Kubo ...................... A61F 5/453 604/350 |
| 5,304,749 | A | 4/1994 | Crandell |
| 5,312,383 | A | 5/1994 | Kubalak |
| 5,318,550 | A | 6/1994 | Cermak et al. |
| 5,330,457 | A | 7/1994 | Cohen |
| 5,330,459 | A | 7/1994 | Lavon et al. |
| 5,334,174 | A | 8/1994 | Street |
| 5,340,840 | A | 8/1994 | Park et al. |
| 5,382,244 | A | 1/1995 | Telang |
| 5,397,315 | A | 3/1995 | Schmidt et al. |
| 5,409,014 | A | 4/1995 | Napoli et al. |
| 5,409,475 | A | 4/1995 | Steer |
| 5,411,495 | A | 5/1995 | Willingham |
| 5,423,784 | A | 6/1995 | Metz |
| 5,423,788 | A | 6/1995 | Rollins et al. |
| 5,437,836 | A | 8/1995 | Yamada |
| 5,456,246 | A | 10/1995 | Schmieding et al. |
| 5,466,229 | A | 11/1995 | Elson et al. |
| 5,478,334 | A | 12/1995 | Bernstein |
| 5,499,977 | A | 3/1996 | Marx |
| 5,543,042 | A | 8/1996 | Filan et al. |
| D373,928 | S | 9/1996 | Green |
| 5,582,604 | A | 12/1996 | Ahr et al. |
| 5,592,950 | A | 1/1997 | Kopelowicz |
| 5,593,389 | A | 1/1997 | Chang |
| 5,605,161 | A | 2/1997 | Cross |
| 5,614,699 | A | 3/1997 | Yashiro et al. |
| 5,618,277 | A | 4/1997 | Goulter |
| 5,628,735 | A | 5/1997 | Skow |
| 5,632,736 | A | 5/1997 | Block |
| 5,636,643 | A | 6/1997 | Argenta et al. |
| 5,637,104 | A | 6/1997 | Ball et al. |
| 5,662,633 | A | 9/1997 | Doak et al. |
| 5,674,212 | A | 10/1997 | Osborn et al. |
| 5,678,564 | A | 10/1997 | Lawrence et al. |
| 5,678,654 | A | 10/1997 | Uzawa |
| 5,681,297 | A | 10/1997 | Hashimoto et al. |
| 5,687,429 | A | 11/1997 | Rahlff |
| 5,695,485 | A | 12/1997 | Duperret et al. |
| 5,700,254 | A | 12/1997 | Mcdowall et al. |
| 5,701,612 | A | 12/1997 | Daneshvar |
| 5,705,777 | A | 1/1998 | Flanigan et al. |
| 5,735,835 | A | 4/1998 | Holland |
| 5,752,944 | A | 5/1998 | Dann et al. |
| 5,763,333 | A | 6/1998 | Suzuki et al. |
| 5,772,644 | A | 6/1998 | Bark et al. |
| 5,792,132 | A | 8/1998 | Garcia |
| 5,827,243 | A | 10/1998 | Palestrant |
| 5,827,247 | A | 10/1998 | Kay |
| 5,827,250 | A | 10/1998 | Fujioka et al. |
| 5,827,257 | A | 10/1998 | Fujioka et al. |
| D401,699 | S | 11/1998 | Herchenbach et al. |
| 5,859,393 | A | 1/1999 | Cummins et al. |
| 5,865,378 | A | 2/1999 | Hollinshead et al. |
| 5,873,869 | A | 2/1999 | Hammons et al. |
| 5,876,393 | A | 3/1999 | Ahr et al. |
| 5,887,291 | A | 3/1999 | Bellizzi |
| 5,891,125 | A | 4/1999 | Plumley |
| 5,894,608 | A | 4/1999 | Birbara |
| 5,895,349 | A | 4/1999 | Tihon |
| D409,303 | S | 5/1999 | Oepping |
| 5,911,222 | A | 6/1999 | Lawrence et al. |
| 5,956,782 | A | 9/1999 | Olguin |
| 5,957,904 | A | 9/1999 | Holland |
| 5,968,026 | A | 10/1999 | Osborn et al. |
| 5,972,505 | A | 10/1999 | Phillips et al. |
| 6,007,526 | A | 12/1999 | Passalaqua et al. |
| 6,039,060 | A | 3/2000 | Rower |
| 6,050,983 | A | 4/2000 | Moore et al. |
| 6,059,762 | A | 5/2000 | Boyer et al. |
| 6,063,064 | A | 5/2000 | Tuckey et al. |
| 6,098,625 | A | 8/2000 | Winkler |
| 6,105,174 | A | 8/2000 | Karlsten et al. |
| 6,113,582 | A | 9/2000 | Dwork |
| 6,117,163 | A | 9/2000 | Bierman |
| 6,123,398 | A | 9/2000 | Arai et al. |
| 6,129,718 | A | 10/2000 | Wada et al. |
| 6,131,964 | A | 10/2000 | Sareshwala |
| 6,152,902 | A | 11/2000 | Christian et al. |
| 6,164,569 | A | 12/2000 | Hollinshead et al. |

(56) References Cited

U.S. PATENT DOCUMENTS

| | | | |
|---|---|---|---|
| 6,177,606 | B1 | 1/2001 | Etheredge et al. |
| 6,209,142 | B1 | 4/2001 | Mattsson et al. |
| 6,220,050 | B1 | 4/2001 | Cooksey |
| 6,244,311 | B1 | 6/2001 | Hand et al. |
| 6,248,096 | B1 | 6/2001 | Dwork et al. |
| 6,263,887 | B1 | 7/2001 | Dunn |
| 6,283,246 | B1 | 9/2001 | Nishikawa |
| 6,296,627 | B1 | 10/2001 | Edwards |
| 6,311,339 | B1 | 11/2001 | Kraus |
| 6,316,688 | B1 | 11/2001 | Hammons et al. |
| 6,336,919 | B1 | 1/2002 | Davis et al. |
| 6,338,729 | B1 | 1/2002 | Wada et al. |
| 6,352,525 | B1 | 3/2002 | Wakabayashi |
| 6,394,988 | B1 | 5/2002 | Hashimoto |
| 6,395,956 | B1 | 5/2002 | Glasgow et al. |
| 6,398,742 | B1 | 6/2002 | Kim |
| 6,406,463 | B1 | 6/2002 | Brown |
| 6,409,712 | B1 | 6/2002 | Dutari et al. |
| 6,415,888 | B2 | 7/2002 | An et al. |
| 6,416,500 | B1 | 7/2002 | Wada et al. |
| 6,423,045 | B1 | 7/2002 | Wise et al. |
| 6,428,521 | B1 | 8/2002 | Droll |
| 6,428,522 | B1 | 8/2002 | Dipalma et al. |
| 6,446,454 | B1 | 9/2002 | Lee et al. |
| 6,461,340 | B1 | 10/2002 | Lenker et al. |
| 6,467,570 | B1 | 10/2002 | Herold |
| 6,475,198 | B1 | 11/2002 | Lipman et al. |
| 6,479,726 | B1 | 11/2002 | Cole et al. |
| 6,491,673 | B1 | 12/2002 | Palumbo et al. |
| 6,508,794 | B1 | 1/2003 | Palumbo et al. |
| 6,524,292 | B1 | 2/2003 | Dipalma et al. |
| 6,540,729 | B1 | 4/2003 | Wada et al. |
| 6,547,771 | B2 | 4/2003 | Robertson et al. |
| 6,551,293 | B1 | 4/2003 | Mitchell |
| 6,569,133 | B2 | 5/2003 | Cheng et al. |
| D476,518 | S | 7/2003 | Doppelt |
| 6,592,560 | B2 | 7/2003 | Snyder et al. |
| 6,610,038 | B1 | 8/2003 | Dipalma et al. |
| 6,618,868 | B2 | 9/2003 | Minnick |
| 6,620,142 | B1 | 9/2003 | Flueckiger |
| 6,629,651 | B1 | 10/2003 | Male et al. |
| 6,635,037 | B1 | 10/2003 | Bennett |
| 6,635,038 | B2 | 10/2003 | Scovel |
| 6,652,495 | B1 | 11/2003 | Walker |
| 6,666,850 | B1 | 12/2003 | Ahr et al. |
| 6,685,684 | B1 | 2/2004 | Falconer |
| 6,695,828 | B1 | 2/2004 | Dipalma et al. |
| 6,699,174 | B1 | 3/2004 | Bennett |
| 6,700,034 | B1 | 3/2004 | Lindsay et al. |
| 6,702,793 | B1 | 3/2004 | Sweetser et al. |
| 6,706,027 | B2 | 3/2004 | Harvie et al. |
| 6,732,384 | B2 | 5/2004 | Scott |
| 6,736,977 | B1 | 5/2004 | Hall et al. |
| 6,740,066 | B2 | 5/2004 | Wolff et al. |
| 6,764,477 | B1 | 7/2004 | Chen et al. |
| 6,783,519 | B2 | 8/2004 | Samuelsson |
| 6,796,974 | B2 | 9/2004 | Palumbo et al. |
| 6,814,547 | B2 | 11/2004 | Childers et al. |
| 6,849,065 | B2 | 2/2005 | Schmidt et al. |
| 6,857,137 | B2 | 2/2005 | Otto |
| 6,885,690 | B2 | 4/2005 | Aggerstam et al. |
| 6,888,044 | B2 | 5/2005 | Fell et al. |
| 6,893,425 | B2 | 5/2005 | Dunn et al. |
| 6,912,737 | B2 | 7/2005 | Ernest et al. |
| 6,918,899 | B2 | 7/2005 | Harvie |
| 6,979,324 | B2 | 12/2005 | Bybordi et al. |
| 7,018,366 | B2 | 3/2006 | Easter |
| 7,066,411 | B2 | 6/2006 | Male et al. |
| 7,122,023 | B1 | 10/2006 | Hinoki |
| 7,125,399 | B2 | 10/2006 | Miskie |
| 7,131,964 | B2 | 11/2006 | Harvie |
| 7,135,012 | B2 | 11/2006 | Harvie |
| 7,141,043 | B2 | 11/2006 | Harvie |
| D533,972 | S | 12/2006 | La |
| 7,160,273 | B2 | 1/2007 | Greter et al. |
| 7,166,092 | B2 | 1/2007 | Elson et al. |
| 7,171,699 | B2 | 2/2007 | Ernest et al. |
| 7,171,871 | B2 | 2/2007 | Kozak |
| 7,179,951 | B2 | 2/2007 | Krishnaswamy-Mirle et al. |
| 7,181,781 | B1 | 2/2007 | Trabold et al. |
| 7,186,245 | B1 | 3/2007 | Cheng et al. |
| 7,192,424 | B2 | 3/2007 | Cooper |
| 7,219,764 | B1 | 5/2007 | Forbes |
| 7,220,250 | B2 | 5/2007 | Suzuki et al. |
| D562,975 | S | 2/2008 | Otto |
| 7,335,189 | B2 | 2/2008 | Harvie |
| 7,358,282 | B2 | 4/2008 | Krueger et al. |
| 7,390,320 | B2 | 6/2008 | Machida et al. |
| 7,438,706 | B2 | 10/2008 | Koizumi et al. |
| 7,488,310 | B2 | 2/2009 | Yang |
| 7,491,194 | B1 | 2/2009 | Oliwa |
| D591,106 | S | 4/2009 | Dominique et al. |
| 7,513,381 | B2 | 4/2009 | Heng et al. |
| 7,520,872 | B2 | 4/2009 | Biggie et al. |
| D593,801 | S | 6/2009 | Wilson et al. |
| 7,540,364 | B2 | 6/2009 | Sanderson |
| 7,549,511 | B2 | 6/2009 | Marocco |
| 7,549,512 | B2 | 6/2009 | Newberry |
| 7,585,293 | B2 | 9/2009 | Vermaak |
| 7,588,560 | B1 | 9/2009 | Dunlop |
| 7,637,905 | B2 | 12/2009 | Saadat et al. |
| 7,658,730 | B2 | 2/2010 | Conley |
| 7,665,359 | B2 | 2/2010 | Barber |
| 7,682,347 | B2 | 3/2010 | Parks et al. |
| 7,687,004 | B2 | 3/2010 | Allen |
| 7,695,459 | B2 | 4/2010 | Gilbert et al. |
| 7,695,460 | B2 | 4/2010 | Wada et al. |
| 7,699,818 | B2 | 4/2010 | Gilbert |
| 7,699,831 | B2 | 4/2010 | Bengtson et al. |
| 7,722,584 | B2 | 5/2010 | Tanaka et al. |
| 7,727,206 | B2 | 6/2010 | Gorres |
| 7,740,620 | B2 | 6/2010 | Gilbert et al. |
| 7,749,205 | B2 | 7/2010 | Tazoe et al. |
| 7,755,497 | B2 | 7/2010 | Wada et al. |
| 7,766,887 | B2 | 8/2010 | Burns et al. |
| 7,803,144 | B1 | 9/2010 | Vollrath |
| D625,407 | S | 10/2010 | Koizumi et al. |
| 7,806,879 | B2 | 10/2010 | Brooks et al. |
| 7,811,272 | B2 | 10/2010 | Lindsay et al. |
| 7,815,067 | B2 | 10/2010 | Matsumoto et al. |
| 7,833,169 | B2 | 11/2010 | Hannon |
| 7,857,806 | B2 | 12/2010 | Karpowicz et al. |
| 7,866,942 | B2 | 1/2011 | Harvie |
| 7,871,385 | B2 | 1/2011 | Levinson et al. |
| 7,875,010 | B2 | 1/2011 | Frazier et al. |
| 7,901,389 | B2 | 3/2011 | Mombrinie |
| 7,927,320 | B2 | 4/2011 | Goldwasser et al. |
| 7,927,321 | B2 | 4/2011 | Marland |
| 7,931,634 | B2 | 4/2011 | Swiecicki et al. |
| 7,939,706 | B2 | 5/2011 | Okabe et al. |
| 7,946,443 | B2 | 5/2011 | Stull et al. |
| 7,947,025 | B2 | 5/2011 | Buglino et al. |
| 7,963,419 | B2 | 6/2011 | Burney et al. |
| 7,976,519 | B2 | 7/2011 | Bubb et al. |
| 7,993,318 | B2 | 8/2011 | Olsson et al. |
| 8,015,627 | B2 | 9/2011 | Baker et al. |
| 8,016,071 | B1 | 9/2011 | Martinus et al. |
| 8,028,460 | B2 | 10/2011 | Williams |
| 8,047,398 | B2 | 11/2011 | Dimartino et al. |
| 8,083,094 | B2 | 12/2011 | Caulfield et al. |
| 8,128,608 | B2 | 3/2012 | Thevenin |
| 8,167,860 | B1 | 5/2012 | Siegel |
| 8,181,651 | B2 | 5/2012 | Pinel |
| 8,181,819 | B2 | 5/2012 | Burney et al. |
| 8,211,063 | B2 | 7/2012 | Bierman et al. |
| 8,221,369 | B2 | 7/2012 | Parks et al. |
| 8,241,262 | B2 | 8/2012 | Mahnensmith |
| 8,277,426 | B2 | 10/2012 | Wilcox et al. |
| 8,287,508 | B1 | 10/2012 | Sanchez |
| 8,303,554 | B2 | 11/2012 | Tsai et al. |
| 8,322,565 | B2 | 12/2012 | Caulfield et al. |
| 8,337,477 | B2 | 12/2012 | Parks et al. |
| D674,241 | S | 1/2013 | Bickert et al. |
| 8,343,122 | B2 | 1/2013 | Gorres |

(56) References Cited

U.S. PATENT DOCUMENTS

| | | | |
|---|---|---|---|
| 8,343,125 | B2 | 1/2013 | Kawazoe et al. |
| 8,353,074 | B2 | 1/2013 | Krebs |
| 8,353,886 | B2 | 1/2013 | Bester et al. |
| D676,241 | S | 2/2013 | Merrill |
| 8,388,587 | B1 | 3/2013 | Gmuer et al. |
| 8,388,588 | B2 | 3/2013 | Wada et al. |
| D679,807 | S | 4/2013 | Burgess et al. |
| 8,425,482 | B2 | 4/2013 | Khoubnazar |
| 8,434,586 | B2 | 5/2013 | Pawelski et al. |
| 8,449,510 | B2 | 5/2013 | Martini et al. |
| D684,260 | S | 6/2013 | Lund et al. |
| 8,470,230 | B2 | 6/2013 | Caulfield et al. |
| 8,479,941 | B2 | 7/2013 | Matsumoto et al. |
| 8,479,949 | B2 | 7/2013 | Henkel |
| 8,500,719 | B1 | 8/2013 | Simpson et al. |
| 8,512,301 | B2 | 8/2013 | Ma |
| 8,529,530 | B2 | 9/2013 | Koch et al. |
| 8,535,284 | B2 | 9/2013 | Joder et al. |
| 8,546,639 | B2 | 10/2013 | Wada et al. |
| 8,551,062 | B2 | 10/2013 | Kay |
| 8,551,075 | B2 | 10/2013 | Bengtson |
| 8,568,376 | B2 | 10/2013 | Delattre et al. |
| D694,404 | S | 11/2013 | Burgess et al. |
| 8,585,683 | B2 | 11/2013 | Bengtson et al. |
| 8,652,112 | B2 | 2/2014 | Johannison et al. |
| 8,669,412 | B2 | 3/2014 | Fernkvist et al. |
| D702,973 | S | 4/2014 | Norland et al. |
| 8,703,032 | B2 | 4/2014 | Menon et al. |
| D704,330 | S | 5/2014 | Cicatelli |
| D704,510 | S | 5/2014 | Mason et al. |
| D705,423 | S | 5/2014 | Walsh Cutler |
| D705,926 | S | 5/2014 | Burgess et al. |
| 8,714,394 | B2 | 5/2014 | Wulf |
| 8,715,267 | B2 | 5/2014 | Bengtson et al. |
| 8,757,425 | B2 | 6/2014 | Copeland |
| 8,777,032 | B2 | 7/2014 | Biesecker et al. |
| 8,808,260 | B2 | 8/2014 | Koch et al. |
| 8,864,730 | B2 | 10/2014 | Conway et al. |
| 8,881,923 | B2 | 11/2014 | Higginson |
| 8,882,731 | B2 | 11/2014 | Suzuki et al. |
| 8,936,585 | B2 | 1/2015 | Carson et al. |
| D729,581 | S | 5/2015 | Boroski |
| 9,028,460 | B2 | 5/2015 | Medeiros |
| 9,056,698 | B2 | 6/2015 | Noer |
| 9,078,792 | B2 | 7/2015 | Ruiz |
| 9,145,879 | B2 | 9/2015 | Pirovano et al. |
| 9,173,602 | B2 | 11/2015 | Gilbert |
| 9,173,799 | B2 | 11/2015 | Tanimoto et al. |
| 9,187,220 | B2 | 11/2015 | Biesecker et al. |
| 9,199,772 | B2 | 12/2015 | Krippendorf |
| 9,233,020 | B2 | 1/2016 | Matsumiya |
| 9,248,058 | B2 | 2/2016 | Conway et al. |
| 9,308,118 | B1 | 4/2016 | Dupree et al. |
| 9,309,029 | B2 | 4/2016 | Incorvia et al. |
| 9,333,281 | B2 | 5/2016 | Giezendanner et al. |
| 9,381,108 | B2 | 7/2016 | Longoni et al. |
| 9,382,047 | B2 | 7/2016 | Schmidtner et al. |
| 9,402,424 | B2 | 8/2016 | Roy |
| 9,456,937 | B2 | 10/2016 | Ellis |
| 9,480,595 | B2 | 11/2016 | Baham et al. |
| 9,517,865 | B2 | 12/2016 | Albers et al. |
| D777,941 | S | 1/2017 | Piramoon |
| 9,533,806 | B2 | 1/2017 | Ding et al. |
| 9,550,611 | B2 | 1/2017 | Hodge |
| 9,555,930 | B2 | 1/2017 | Campbell et al. |
| 9,623,159 | B2 | 4/2017 | Locke |
| D789,522 | S | 6/2017 | Burgess et al. |
| 9,687,849 | B2 | 6/2017 | Bruno et al. |
| 9,694,949 | B2 | 7/2017 | Hendricks et al. |
| 9,709,048 | B2 | 7/2017 | Kinjo |
| 9,713,547 | B2 | 7/2017 | Lee et al. |
| 9,732,754 | B2 | 8/2017 | Huang et al. |
| 9,737,433 | B2 | 8/2017 | Joh |
| 9,752,564 | B2 | 9/2017 | Arceno et al. |
| 9,788,992 | B2 | 10/2017 | Harvie |
| D804,907 | S | 12/2017 | Sandoval |
| 9,868,564 | B2 | 1/2018 | McGirr et al. |
| D814,239 | S | 4/2018 | Arora |
| D817,484 | S | 5/2018 | Lafond |
| 9,968,908 | B2 | 5/2018 | Ladrech et al. |
| 10,010,393 | B1 | 7/2018 | Nguyen et al. |
| 10,037,640 | B2 | 7/2018 | Gordon |
| 10,058,470 | B2 | 8/2018 | Phillips |
| 10,098,990 | B2 | 10/2018 | Koch et al. |
| D835,264 | S | 12/2018 | Mozzicato et al. |
| D835,779 | S | 12/2018 | Mozzicato et al. |
| D840,533 | S | 2/2019 | Mozzicato et al. |
| D840,534 | S | 2/2019 | Mozzicato et al. |
| 10,225,376 | B2 | 3/2019 | Perez Martinez |
| 10,226,376 | B2 | 3/2019 | Sanchez et al. |
| 10,258,517 | B1 | 4/2019 | Maschino et al. |
| D848,612 | S | 5/2019 | Mozzicato et al. |
| 10,307,305 | B1 | 6/2019 | Hodges |
| 10,335,121 | B2 | 7/2019 | Desai |
| D856,512 | S | 8/2019 | Cowart et al. |
| 10,376,406 | B2 | 8/2019 | Newton |
| 10,376,407 | B2 | 8/2019 | Newton |
| 10,390,989 | B2 | 8/2019 | Sanchez et al. |
| D858,144 | S | 9/2019 | Fu |
| 10,406,039 | B2 | 9/2019 | Villarreal |
| 10,407,222 | B2 | 9/2019 | Allen |
| 10,478,356 | B2 | 11/2019 | Griffin |
| 10,500,108 | B1 | 12/2019 | Maschino et al. |
| 10,502,198 | B2 | 12/2019 | Stumpf et al. |
| 10,538,366 | B2 | 1/2020 | Pentelovitch et al. |
| 10,569,938 | B2 | 2/2020 | Zhao et al. |
| 10,577,156 | B2 | 3/2020 | Dagnelie et al. |
| RE47,930 | E | 4/2020 | Cho |
| 10,618,721 | B2 | 4/2020 | Vazin |
| D884,390 | S | 5/2020 | Wang |
| 10,669,079 | B2 | 6/2020 | Freedman et al. |
| D892,315 | S | 8/2020 | Airy |
| 10,730,672 | B2 | 8/2020 | Bertram et al. |
| 10,737,848 | B2 | 8/2020 | Philip et al. |
| 10,765,854 | B2 | 9/2020 | Law et al. |
| 10,766,670 | B2 | 9/2020 | Kittmann |
| 10,799,386 | B1 | 10/2020 | Harrison |
| 10,806,642 | B2 | 10/2020 | Tagomori et al. |
| D901,214 | S | 11/2020 | Hu |
| 10,849,799 | B2 | 12/2020 | Nishikawa et al. |
| 10,857,025 | B2 | 12/2020 | Davis et al. |
| 10,865,017 | B1 | 12/2020 | Cowart et al. |
| 10,889,412 | B2 | 1/2021 | West et al. |
| 10,913,581 | B2 | 2/2021 | Stahlecker |
| D912,244 | S | 3/2021 | Rehm et al. |
| 10,952,889 | B2 | 3/2021 | Newton et al. |
| 10,973,378 | B2 | 4/2021 | Ryu et al. |
| 10,973,678 | B2 | 4/2021 | Newton et al. |
| 10,974,874 | B2 | 4/2021 | Ragias et al. |
| 11,000,401 | B2 | 5/2021 | Ecklund et al. |
| 11,002,165 | B2 | 5/2021 | Poulin |
| D923,365 | S | 6/2021 | Wang |
| 11,026,829 | B2 | 6/2021 | Harvie |
| 11,027,900 | B2 | 6/2021 | Liu |
| 11,045,346 | B2 | 6/2021 | Argent et al. |
| D928,946 | S | 8/2021 | Sanchez et al. |
| 11,090,183 | B2 | 8/2021 | Sanchez et al. |
| 11,160,695 | B2 | 11/2021 | Febo et al. |
| 11,160,697 | B2 | 11/2021 | Maschino et al. |
| 11,168,420 | B2 | 11/2021 | Kinugasa et al. |
| 11,179,506 | B2 | 11/2021 | Barr et al. |
| 11,199,116 | B2 | 12/2021 | Ostromecki et al. |
| 11,207,206 | B2 | 12/2021 | Sharma et al. |
| 11,226,376 | B2 | 1/2022 | Yamauchi et al. |
| 11,253,389 | B2 | 2/2022 | Sharma et al. |
| 11,253,407 | B2 | 2/2022 | Miao et al. |
| 11,326,586 | B2 | 5/2022 | Milner et al. |
| 11,369,508 | B2 | 6/2022 | Ecklund et al. |
| 11,369,524 | B2 | 6/2022 | Hubbard et al. |
| 11,376,152 | B2 | 7/2022 | Sanchez et al. |
| 11,382,786 | B2 | 7/2022 | Sanchez et al. |
| 11,382,788 | B2 | 7/2022 | Hjorth et al. |
| 11,389,318 | B2 | 7/2022 | Radl et al. |
| 11,395,871 | B2 | 7/2022 | Radl et al. |

(56) References Cited

U.S. PATENT DOCUMENTS

| | | | |
|---|---|---|---|
| 11,399,990 | B2 | 8/2022 | Suyama |
| 11,426,303 | B2 | 8/2022 | Davis et al. |
| 11,504,265 | B2 | 11/2022 | Godinez et al. |
| 11,529,252 | B2 | 12/2022 | Glithero et al. |
| 11,547,788 | B2 | 1/2023 | Radl et al. |
| 11,806,266 | B2 | 11/2023 | Sanchez et al. |
| 11,839,567 | B2 | 12/2023 | Davis et al. |
| D1,010,109 | S | 1/2024 | Ecklund et al. |
| 11,857,716 | B2 | 1/2024 | Lee et al. |
| 11,865,030 | B2 | 1/2024 | Davis et al. |
| 11,890,221 | B2 | 2/2024 | Ulreich et al. |
| 11,911,160 | B2 | 2/2024 | Woodard et al. |
| 11,925,575 | B2 | 3/2024 | Newton |
| 11,938,053 | B2 * | 3/2024 | Austermann ........... A61F 5/455 |
| 11,944,740 | B2 | 4/2024 | Hughett et al. |
| 11,994,122 | B2 | 5/2024 | Bodain |
| 11,998,475 | B2 | 6/2024 | Becker et al. |
| 12,023,457 | B2 | 7/2024 | Mann et al. |
| 12,042,422 | B2 | 7/2024 | Davis et al. |
| D1,038,385 | S | 8/2024 | Ecklund et al. |
| 12,064,372 | B2 | 8/2024 | Godinez et al. |
| 12,070,432 | B2 | 8/2024 | Tourchak et al. |
| 12,090,083 | B2 | 9/2024 | Ecklund et al. |
| 12,133,813 | B2 | 11/2024 | Ulreich et al. |
| 12,138,195 | B2 | 11/2024 | Alder et al. |
| 12,186,229 | B2 | 1/2025 | Davis et al. |
| 12,245,966 | B2 | 3/2025 | Newton |
| 2001/0037097 | A1 | 11/2001 | Cheng et al. |
| 2001/0037098 | A1 | 11/2001 | Snyder |
| 2001/0054426 | A1 | 12/2001 | Knudson et al. |
| 2002/0019614 | A1 | 2/2002 | Woon |
| 2002/0026161 | A1 | 2/2002 | Grundke |
| 2002/0026163 | A1 | 2/2002 | Grundke |
| 2002/0042945 | A1 | 4/2002 | Sands |
| 2002/0087131 | A1 | 7/2002 | Wolff et al. |
| 2002/0091364 | A1 | 7/2002 | Prabhakar |
| 2002/0189992 | A1 | 12/2002 | Schmidt et al. |
| 2002/0193760 | A1 | 12/2002 | Thompson |
| 2002/0193762 | A1 | 12/2002 | Suydam |
| 2003/0004436 | A1 | 1/2003 | Schmidt et al. |
| 2003/0032931 | A1 | 2/2003 | Grundke et al. |
| 2003/0032944 | A1 | 2/2003 | Cawood |
| 2003/0073964 | A1 | 4/2003 | Palumbo et al. |
| 2003/0074724 | A1 | 4/2003 | Sands |
| 2003/0120178 | A1 | 6/2003 | Heki |
| 2003/0129178 | A1 | 7/2003 | Wegman et al. |
| 2003/0157859 | A1 | 8/2003 | Ishikawa |
| 2003/0181880 | A1 | 9/2003 | Schwartz |
| 2003/0195484 | A1 | 10/2003 | Harvie |
| 2003/0204173 | A1 | 10/2003 | Burns et al. |
| 2003/0233079 | A1 | 12/2003 | Parks et al. |
| 2004/0006321 | A1 | 1/2004 | Cheng et al. |
| 2004/0015141 | A1 | 1/2004 | Cheng et al. |
| 2004/0056122 | A1 | 3/2004 | Male et al. |
| 2004/0084465 | A1 | 5/2004 | Luburic |
| 2004/0127872 | A1 | 7/2004 | Petryk et al. |
| 2004/0128749 | A1 | 7/2004 | Scott |
| 2004/0143229 | A1 | 7/2004 | Easter |
| 2004/0147863 | A1 | 7/2004 | Diaz et al. |
| 2004/0147894 | A1 | 7/2004 | Mizutani et al. |
| 2004/0147895 | A1 | 7/2004 | Mizutani et al. |
| 2004/0158221 | A1 | 8/2004 | Mizutani et al. |
| 2004/0176731 | A1 | 9/2004 | Cheng et al. |
| 2004/0176746 | A1 | 9/2004 | Forral |
| 2004/0181201 | A1 | 9/2004 | Mizutani et al. |
| 2004/0191919 | A1 | 9/2004 | Unger et al. |
| 2004/0194792 | A1 | 10/2004 | Zhuang et al. |
| 2004/0200936 | A1 | 10/2004 | Opperthauser |
| 2004/0207530 | A1 | 10/2004 | Nielsen |
| 2004/0236292 | A1 | 11/2004 | Tazoe et al. |
| 2004/0243075 | A1 | 12/2004 | Harvie |
| 2004/0254547 | A1 | 12/2004 | Okabe et al. |
| 2005/0010182 | A1 | 1/2005 | Parks et al. |
| 2005/0010197 | A1 | 1/2005 | Lau et al. |
| 2005/0033248 | A1 | 2/2005 | Machida et al. |
| 2005/0065471 | A1 | 3/2005 | Kuntz |
| 2005/0070861 | A1 | 3/2005 | Okabe et al. |
| 2005/0070862 | A1 | 3/2005 | Tazoe et al. |
| 2005/0082300 | A1 | 4/2005 | Modrell et al. |
| 2005/0097662 | A1 | 5/2005 | Leimkuhler et al. |
| 2005/0101924 | A1 | 5/2005 | Elson et al. |
| 2005/0119630 | A1 | 6/2005 | Harvie |
| 2005/0131361 | A1 | 6/2005 | Miskie |
| 2005/0137557 | A1 | 6/2005 | Swiecicki et al. |
| 2005/0137560 | A1 | 6/2005 | Mizutani et al. |
| 2005/0137561 | A1 | 6/2005 | Mizutani et al. |
| 2005/0154360 | A1 | 7/2005 | Harvie |
| 2005/0177070 | A1 | 8/2005 | Levinson et al. |
| 2005/0197639 | A1 | 9/2005 | Mombrinie |
| 2005/0197645 | A1 | 9/2005 | Karpowicz et al. |
| 2005/0215969 | A1 | 9/2005 | Mizutani et al. |
| 2005/0273069 | A1 | 12/2005 | Mizutani et al. |
| 2005/0273920 | A1 | 12/2005 | Marinas |
| 2005/0277903 | A1 | 12/2005 | Mizutani et al. |
| 2005/0277904 | A1 | 12/2005 | Chase et al. |
| 2005/0279359 | A1 | 12/2005 | Leblanc et al. |
| 2006/0004332 | A1 | 1/2006 | Marx |
| 2006/0015080 | A1 | 1/2006 | Mahnensmith |
| 2006/0015081 | A1 | 1/2006 | Suzuki et al. |
| 2006/0016778 | A1 | 1/2006 | Park |
| 2006/0069359 | A1 | 3/2006 | Dipalma et al. |
| 2006/0079854 | A1 | 4/2006 | Kay et al. |
| 2006/0111648 | A1 | 5/2006 | Vermaak |
| 2006/0113334 | A1 | 6/2006 | Mikhail et al. |
| 2006/0155214 | A1 | 7/2006 | Wightman |
| 2006/0171997 | A1 | 8/2006 | Gruenbacher et al. |
| 2006/0180566 | A1 | 8/2006 | Mataya |
| 2006/0200102 | A1 | 9/2006 | Cooper |
| 2006/0229575 | A1 | 10/2006 | Boiarski |
| 2006/0229576 | A1 | 10/2006 | Conway et al. |
| 2006/0231648 | A1 | 10/2006 | Male et al. |
| 2006/0235266 | A1 | 10/2006 | Nan |
| 2006/0235359 | A1 | 10/2006 | Marland |
| 2006/0241553 | A1 | 10/2006 | Harvie |
| 2006/0269439 | A1 | 11/2006 | White |
| 2006/0277670 | A1 | 12/2006 | Baker et al. |
| 2007/0006368 | A1 | 1/2007 | Key et al. |
| 2007/0010797 | A1 | 1/2007 | Nishtala et al. |
| 2007/0016152 | A1 | 1/2007 | Karpowicz et al. |
| 2007/0025886 | A1 * | 2/2007 | Yong ....................... B01L 3/502 422/400 |
| 2007/0038194 | A1 | 2/2007 | Wada et al. |
| 2007/0055209 | A1 | 3/2007 | Patel et al. |
| 2007/0073252 | A1 | 3/2007 | Forgrave |
| 2007/0117880 | A1 | 5/2007 | Elson et al. |
| 2007/0118993 | A1 | 5/2007 | Bates |
| 2007/0135786 | A1 | 6/2007 | Schmidt et al. |
| 2007/0137718 | A1 | 6/2007 | Rushlander et al. |
| 2007/0149935 | A1 | 6/2007 | Dirico |
| 2007/0191804 | A1 | 8/2007 | Coley |
| 2007/0203464 | A1 | 8/2007 | Green et al. |
| 2007/0214553 | A1 | 9/2007 | Carromba et al. |
| 2007/0225663 | A1 | 9/2007 | Watt et al. |
| 2007/0225666 | A1 | 9/2007 | Otto |
| 2007/0225668 | A1 | 9/2007 | Otto |
| 2007/0266486 | A1 | 11/2007 | Ramirez |
| 2007/0282309 | A1 | 12/2007 | Bengtson et al. |
| 2008/0004576 | A1 | 1/2008 | Tanaka et al. |
| 2008/0015526 | A1 | 1/2008 | Reiner et al. |
| 2008/0015527 | A1 | 1/2008 | House |
| 2008/0033386 | A1 | 2/2008 | Okabe et al. |
| 2008/0041869 | A1 | 2/2008 | Backaert |
| 2008/0077099 | A1 | 3/2008 | House |
| 2008/0091153 | A1 | 4/2008 | Harvie |
| 2008/0091158 | A1 | 4/2008 | Yang |
| 2008/0114327 | A1 | 5/2008 | Barge |
| 2008/0167634 | A1 | 7/2008 | Kouta et al. |
| 2008/0183157 | A1 | 7/2008 | Walters |
| 2008/0215031 | A1 | 9/2008 | Belfort et al. |
| 2008/0234642 | A1 | 9/2008 | Patterson et al. |
| 2008/0269703 | A1 | 10/2008 | Collins et al. |
| 2008/0281282 | A1 | 11/2008 | Finger et al. |
| 2008/0287894 | A1 | 11/2008 | Van Den Heuvel et al. |
| 2008/0312550 | A1 | 12/2008 | Nishtala et al. |

(56) References Cited

U.S. PATENT DOCUMENTS

2009/0025717 A1 1/2009 Pinel
2009/0048570 A1 2/2009 Jensen
2009/0056003 A1 3/2009 Ivie et al.
2009/0069761 A1 3/2009 Vogel
2009/0069765 A1 3/2009 Wortham
2009/0120179 A1 5/2009 Nylander et al.
2009/0192482 A1 7/2009 Dodge et al.
2009/0226541 A1 9/2009 Scholz et al.
2009/0234312 A1 9/2009 Otoole et al.
2009/0251510 A1 10/2009 Noro et al.
2009/0259206 A1 10/2009 Kai et al.
2009/0264840 A1 10/2009 Virginio
2009/0270822 A1 10/2009 Medeiros
2009/0281510 A1 11/2009 Fisher
2009/0283982 A1 11/2009 Thomas
2009/0306610 A1 12/2009 Van Den Heuvel et al.
2010/0004612 A1 1/2010 Thevenin
2010/0031429 A1 2/2010 Kim et al.
2010/0032789 A1 2/2010 Schoen et al.
2010/0058660 A1 3/2010 Williams
2010/0121289 A1 5/2010 Parks et al.
2010/0158168 A1 6/2010 Murthy et al.
2010/0160882 A1 6/2010 Lowe
2010/0174250 A1 7/2010 Hu et al.
2010/0179493 A1 7/2010 Heagle et al.
2010/0185168 A1 7/2010 Graauw et al.
2010/0198172 A1 8/2010 Wada et al.
2010/0211032 A1 8/2010 Tsai et al.
2010/0234820 A1 9/2010 Tsai et al.
2010/0241104 A1 9/2010 Gilbert
2010/0263113 A1 10/2010 Shelton et al.
2010/0310845 A1 12/2010 Bond et al.
2011/0028920 A1 2/2011 Johannison
2011/0028922 A1 2/2011 Kay et al.
2011/0034889 A1 2/2011 Smith
2011/0036837 A1 2/2011 Shang
2011/0040267 A1 2/2011 Wada et al.
2011/0040271 A1 2/2011 Rogers et al.
2011/0054426 A1 3/2011 Stewart et al.
2011/0060299 A1 3/2011 Wada et al.
2011/0060300 A1 3/2011 Weig et al.
2011/0077495 A1 3/2011 Gilbert
2011/0077606 A1 3/2011 Wilcox et al.
2011/0087337 A1 4/2011 Forsell
2011/0137273 A1 6/2011 Muellejans et al.
2011/0145993 A1 6/2011 Rader et al.
2011/0152802 A1 6/2011 Dicamillo et al.
2011/0164147 A1 7/2011 Takahashi et al.
2011/0172620 A1 7/2011 Khambatta
2011/0172625 A1 7/2011 Wada et al.
2011/0198904 A1 8/2011 Thomas et al.
2011/0202024 A1 8/2011 Cozzens
2011/0238023 A1 9/2011 Slayton
2011/0240648 A1 10/2011 Tucker
2011/0251572 A1 10/2011 Nishtala et al.
2011/0265889 A1 11/2011 Tanaka et al.
2011/0276020 A1 11/2011 Mitsui
2012/0029452 A1 2/2012 Roedsten
2012/0035577 A1 2/2012 Tomes et al.
2012/0041400 A1 2/2012 Christensen
2012/0059328 A1 3/2012 Dikeman et al.
2012/0066825 A1 3/2012 Birbara et al.
2012/0103347 A1 5/2012 Wheaton et al.
2012/0116336 A1 5/2012 Sharma et al.
2012/0137420 A1 6/2012 Gordon et al.
2012/0165768 A1 6/2012 Sekiyama et al.
2012/0165786 A1 6/2012 Chappa et al.
2012/0209216 A1 8/2012 Jensen et al.
2012/0210503 A1 8/2012 Anzivino et al.
2012/0233761 A1 9/2012 Huang
2012/0245541 A1 9/2012 Suzuki et al.
2012/0245542 A1 9/2012 Suzuki et al.
2012/0245547 A1 9/2012 Wilcox et al.
2012/0253303 A1 10/2012 Suzuki et al.
2012/0271259 A1 10/2012 Ulert
2012/0296305 A1 11/2012 Barraza Khaled et al.
2012/0316522 A1 12/2012 Carter et al.
2012/0330256 A1 12/2012 Wilcox et al.
2013/0006206 A1 1/2013 Wada et al.
2013/0019374 A1 1/2013 Schwartz
2013/0045651 A1 2/2013 Esteves et al.
2013/0053804 A1 2/2013 Soerensen et al.
2013/0096523 A1 4/2013 Chang et al.
2013/0110059 A1 5/2013 Kossow et al.
2013/0138064 A1 5/2013 Stroebech et al.
2013/0150813 A1 6/2013 Gordon et al.
2013/0165880 A1 6/2013 Amos et al.
2013/0218112 A1 8/2013 Thompson
2013/0245496 A1* 9/2013 Wells ................ A61M 25/0017 600/581
2013/0245586 A1 9/2013 Jha
2013/0292537 A1 11/2013 Dirico
2013/0330501 A1 12/2013 Aizenberg et al.
2014/0005647 A1 1/2014 Shuffler et al.
2014/0031774 A1 1/2014 Bengtson
2014/0039432 A1 2/2014 Dunbar et al.
2014/0039440 A1 2/2014 Doescher
2014/0058347 A1 2/2014 Marquette
2014/0107599 A1 4/2014 Fink et al.
2014/0157499 A1 6/2014 Suzuki et al.
2014/0171889 A1 6/2014 Hopman et al.
2014/0182051 A1 7/2014 Tanimoto et al.
2014/0196189 A1 7/2014 Lee et al.
2014/0276501 A1 9/2014 Cisko
2014/0303582 A1 10/2014 Wright et al.
2014/0316381 A1 10/2014 Reglin
2014/0325746 A1 11/2014 Block
2014/0348139 A1 11/2014 Gomez Martinez
2014/0352050 A1 12/2014 Yao et al.
2014/0371628 A1 12/2014 Desai
2015/0045757 A1 2/2015 Lee et al.
2015/0047114 A1 2/2015 Ramirez
2015/0048089 A1 2/2015 Robertson
2015/0135423 A1 5/2015 Sharpe et al.
2015/0157300 A1 6/2015 Ealovega et al.
2015/0209188 A1 7/2015 Scheremet et al.
2015/0209194 A1 7/2015 Heyman
2015/0267862 A1 9/2015 Mishler
2015/0290425 A1 10/2015 Macy et al.
2015/0320583 A1 11/2015 Harvie
2015/0329255 A1 11/2015 Rzepecki
2015/0342799 A1 12/2015 Michiels et al.
2015/0359660 A1 12/2015 Harvie
2015/0359996 A1 12/2015 Arora et al.
2015/0366699 A1 12/2015 Nelson
2016/0029998 A1 2/2016 Brister et al.
2016/0030228 A1 2/2016 Jones
2016/0038356 A1 2/2016 Yao et al.
2016/0051395 A1 2/2016 Ugarte
2016/0058322 A1 3/2016 Brister et al.
2016/0060001 A1 3/2016 Wada et al.
2016/0100976 A1 4/2016 Conway et al.
2016/0106604 A1 4/2016 Timm
2016/0113809 A1 4/2016 Kim
2016/0136338 A1 5/2016 Lee et al.
2016/0183689 A1 6/2016 Miner
2016/0256022 A1 9/2016 Le
2016/0270982 A1 9/2016 Raycheck et al.
2016/0278662 A1 9/2016 Brister et al.
2016/0357400 A1 12/2016 Penha et al.
2016/0366699 A1 12/2016 Zhang et al.
2016/0367226 A1 12/2016 Newton et al.
2016/0367411 A1 12/2016 Justiz et al.
2016/0367726 A1 12/2016 Gratzer
2016/0374848 A1 12/2016 Sanchez et al.
2017/0007438 A1 1/2017 Harvie
2017/0014560 A1 1/2017 Minskoff et al.
2017/0042724 A1 2/2017 Ugarte
2017/0042748 A1 2/2017 Griffin
2017/0100276 A1 4/2017 Joh
2017/0107312 A1 4/2017 Hinayama et al.
2017/0128638 A1 5/2017 Giezendanner et al.
2017/0136209 A1 5/2017 Burnett et al.
2017/0143534 A1 5/2017 Sanchez

(56) References Cited

U.S. PATENT DOCUMENTS

2017/0165100 A1 6/2017 Jackson et al.
2017/0165405 A1 6/2017 Muser et al.
2017/0189225 A1 7/2017 Voorhees et al.
2017/0202692 A1 7/2017 Laniado
2017/0216081 A1 8/2017 Accosta
2017/0238911 A1 8/2017 Duval
2017/0246026 A1 8/2017 Laniado
2017/0252014 A1 9/2017 Siller Gonzalez et al.
2017/0252202 A9 9/2017 Sanchez et al.
2017/0266031 A1* 9/2017 Sanchez .................. A61F 5/443
2017/0266658 A1 9/2017 Bruno et al.
2017/0281399 A1 10/2017 Vanmiddendorp et al.
2017/0281419 A1 10/2017 Pintado
2017/0312116 A1 11/2017 Laniado
2017/0325788 A1 11/2017 Ealovega et al.
2017/0333244 A1 11/2017 Laniado
2017/0348139 A1 12/2017 Newton et al.
2017/0354532 A1 12/2017 Holt
2017/0354551 A1 12/2017 Gawley et al.
2017/0367873 A1 12/2017 Grannum
2018/0002075 A1 1/2018 Lee
2018/0008451 A1 1/2018 Stroebech
2018/0008804 A1 1/2018 Laniado
2018/0021218 A1 1/2018 Brosch et al.
2018/0028349 A1 2/2018 Newton et al.
2018/0037384 A1 2/2018 Archeny et al.
2018/0049910 A1 2/2018 Newton
2018/0064572 A1 3/2018 Wiltshire
2018/0104131 A1 4/2018 Killian
2018/0127187 A1 5/2018 Sewell
2018/0193215 A1 7/2018 Davies et al.
2018/0200101 A1 7/2018 Su
2018/0228642 A1* 8/2018 Davis ..................... A61B 5/208
2018/0256384 A1 9/2018 Kasirye
2018/0271694 A1 9/2018 Fernandez et al.
2018/0317892 A1 11/2018 Catlin
2018/0325748 A1 11/2018 Sharma et al.
2019/0001030 A1 1/2019 Braga et al.
2019/0021899 A1 1/2019 Vlet
2019/0038451 A1 2/2019 Harvie
2019/0046102 A1 2/2019 Kushnir et al.
2019/0059938 A1 2/2019 Holsten
2019/0091059 A1 3/2019 Gabriel
2019/0100362 A1 4/2019 Meyers et al.
2019/0133126 A1 5/2019 Modak et al.
2019/0133814 A1 5/2019 Tammen et al.
2019/0142624 A1* 5/2019 Sanchez .................. A61F 5/453
604/319
2019/0224036 A1 7/2019 Sanchez et al.
2019/0226189 A1 7/2019 Braxton
2019/0240079 A1 8/2019 Tuli
2019/0247222 A1 8/2019 Ecklund et al.
2019/0247223 A1 8/2019 Brun et al.
2019/0247623 A1 8/2019 Helm et al.
2019/0282391 A1 9/2019 Johannes et al.
2019/0314189 A1 10/2019 Acosta
2019/0314190 A1 10/2019 Sanchez et al.
2019/0321587 A1 10/2019 Mcmenamin et al.
2019/0344934 A1 11/2019 Faerber et al.
2019/0365303 A1 12/2019 Bullington et al.
2019/0365307 A1 12/2019 Laing et al.
2019/0365561 A1 12/2019 Newton et al.
2019/0374373 A1 12/2019 Joh
2020/0008985 A1 1/2020 Nguyen et al.
2020/0016012 A1 1/2020 Dutkiewicz
2020/0030595 A1 1/2020 Boukidjian et al.
2020/0046544 A1 2/2020 Godinez et al.
2020/0055638 A1 2/2020 Lau et al.
2020/0070392 A1 3/2020 Huber et al.
2020/0085609 A1 3/2020 Schelch et al.
2020/0085610 A1 3/2020 Cohn et al.
2020/0086090 A1 3/2020 Von Weymarn-schärli et al.
2020/0107518 A1 4/2020 Hiroshima et al.
2020/0129322 A1 4/2020 Leuckel
2020/0171217 A9 6/2020 Braga et al.
2020/0179177 A1 6/2020 Erdem et al.
2020/0187918 A1 6/2020 Wiygul
2020/0206015 A1 7/2020 Langer
2020/0206039 A1 7/2020 Mclain
2020/0214910 A1 7/2020 Varona et al.
2020/0216898 A1 7/2020 Hubbell
2020/0216989 A1 7/2020 Kinugasa et al.
2020/0229964 A1 7/2020 Staali et al.
2020/0231343 A1 7/2020 Freedman et al.
2020/0232841 A1 7/2020 Satish et al.
2020/0246172 A1 8/2020 Ho
2020/0246203 A1 8/2020 Tulk et al.
2020/0255189 A1 8/2020 Liu
2020/0261280 A1 8/2020 Heyman
2020/0276046 A1 9/2020 Staali et al.
2020/0306075 A1 10/2020 Newton et al.
2020/0315837 A1 10/2020 Radl et al.
2020/0315838 A1 10/2020 Eckert
2020/0315872 A1 10/2020 Viens et al.
2020/0315874 A1 10/2020 Viens et al.
2020/0331672 A1 10/2020 Bertram et al.
2020/0345332 A1 11/2020 Duval
2020/0353135 A1 11/2020 Gregory et al.
2020/0367677 A1 11/2020 Silsby et al.
2020/0369444 A1 11/2020 Silsby et al.
2020/0375781 A1 12/2020 Staali et al.
2020/0375810 A1 12/2020 Carlin et al.
2020/0384242 A1 12/2020 Havard et al.
2020/0385179 A1 12/2020 McCourt
2020/0390591 A1 12/2020 Glithero et al.
2020/0390592 A1 12/2020 Merrill
2020/0405521 A1 12/2020 Glasroe
2021/0008771 A1 1/2021 Huber et al.
2021/0009323 A1 1/2021 Markarian et al.
2021/0020072 A1 1/2021 Moehring et al.
2021/0023279 A1 1/2021 Radl et al.
2021/0059853 A1 3/2021 Davis et al.
2021/0061523 A1 3/2021 Bytheway
2021/0069005 A1 3/2021 Sanchez et al.
2021/0069008 A1 3/2021 Blabas et al.
2021/0069009 A1 3/2021 Im
2021/0069030 A1 3/2021 Nishikawa et al.
2021/0077993 A1 3/2021 Nazareth et al.
2021/0113749 A1 4/2021 Radl et al.
2021/0121318 A1 4/2021 Pinlac
2021/0137724 A1 5/2021 Ecklund et al.
2021/0138190 A1 5/2021 Erbey et al.
2021/0154055 A1 5/2021 Villarreal
2021/0170079 A1 6/2021 Radl et al.
2021/0178390 A1 6/2021 Oueslati et al.
2021/0186742 A1 6/2021 Newton et al.
2021/0211568 A1 7/2021 Zhou et al.
2021/0212865 A1 7/2021 Wallajapet et al.
2021/0220162 A1 7/2021 Jamison
2021/0220163 A1 7/2021 Mayrand
2021/0228400 A1 7/2021 Glithero
2021/0228401 A1 7/2021 Becker et al.
2021/0228795 A1 7/2021 Hughett et al.
2021/0229877 A1 7/2021 Ragias et al.
2021/0236323 A1 8/2021 Austermann et al.
2021/0236324 A1 8/2021 Sweeney
2021/0251814 A1 8/2021 Jönegren et al.
2021/0267787 A1 9/2021 Nazemi
2021/0275343 A1 9/2021 Sanchez et al.
2021/0275344 A1 9/2021 Wing
2021/0290454 A1 9/2021 Yamada
2021/0315726 A1 10/2021 Lin
2021/0315727 A1 10/2021 Jiang
2021/0353449 A1 11/2021 Sharma et al.
2021/0353450 A1 11/2021 Sharma et al.
2021/0361469 A1 11/2021 Liu et al.
2021/0369495 A1 12/2021 Cheng et al.
2021/0386925 A1 12/2021 Hartwell et al.
2021/0393433 A1 12/2021 Godinez et al.
2022/0023091 A1 1/2022 Ecklund et al.
2022/0031290 A1 2/2022 Weed
2022/0031523 A1 2/2022 Pierpoint
2022/0039995 A1 2/2022 Johannes et al.
2022/0047410 A1 2/2022 Walthall

(56) References Cited

U.S. PATENT DOCUMENTS

2022/0062027 A1 3/2022 Mitchell et al.
2022/0062028 A1 3/2022 Mitchell et al.
2022/0062029 A1 3/2022 Johannes et al.
2022/0066825 A1 3/2022 Saraf et al.
2022/0071811 A1 3/2022 Cheng et al.
2022/0071826 A1 3/2022 Kulkarni et al.
2022/0104965 A1 4/2022 Vaninetti et al.
2022/0104976 A1 4/2022 Hoeger et al.
2022/0104981 A1 4/2022 Jones
2022/0117773 A1 4/2022 Davis et al.
2022/0117774 A1 4/2022 Meyer et al.
2022/0117775 A1 4/2022 Jones et al.
2022/0118165 A1 4/2022 Knapp et al.
2022/0133524 A1 5/2022 Davis
2022/0151817 A1 5/2022 Mann
2022/0160949 A1 5/2022 Simiele et al.
2022/0168159 A1 6/2022 Triado et al.
2022/0193312 A1 6/2022 Lee et al.
2022/0211536 A1 7/2022 Johannes et al.
2022/0218510 A1 7/2022 Metzger et al.
2022/0229053 A1 7/2022 Levin et al.
2022/0241106 A1 8/2022 Johannes et al.
2022/0248836 A1 8/2022 Cagle et al.
2022/0257407 A1 8/2022 Johannes et al.
2022/0265460 A1 8/2022 Coker
2022/0265462 A1 8/2022 Alder et al.
2022/0270711 A1 8/2022 Feala et al.
2022/0273482 A1 9/2022 Johannes et al.
2022/0280357 A1 9/2022 Jagannathan et al.
2022/0280710 A1 9/2022 Agrawal et al.
2022/0287689 A1 9/2022 Johannes
2022/0287867 A1 9/2022 Jones et al.
2022/0287868 A1 9/2022 Garvey et al.
2022/0296408 A1 9/2022 Evans et al.
2022/0305191 A1 9/2022 Joseph et al.
2022/0313222 A1 10/2022 Austermann et al.
2022/0313474 A1 10/2022 Kriscovich et al.
2022/0331170 A1 10/2022 Erdem et al.
2022/0339023 A1 10/2022 Davis et al.
2022/0339024 A1 10/2022 Johannes et al.
2022/0354685 A1 11/2022 Davis et al.
2022/0362049 A1 11/2022 Austermann et al.
2022/0370231 A1 11/2022 Wang et al.
2022/0370234 A1 11/2022 Hughett et al.
2022/0370235 A1 11/2022 Johannes et al.
2022/0370237 A1 11/2022 Parmar et al.
2022/0387001 A1 12/2022 Askenazi et al.
2022/0387693 A1 12/2022 Bannwart et al.
2022/0395390 A1 12/2022 Brooks
2022/0395391 A1 12/2022 Saunders et al.
2022/0401252 A1 12/2022 Warren
2022/0409419 A1 12/2022 Garvey et al.
2022/0409422 A1 12/2022 Schneider et al.
2023/0018845 A1 1/2023 Lee
2023/0020563 A1 1/2023 Sharma et al.
2023/0031640 A1 2/2023 Hughett et al.
2023/0037159 A1 2/2023 Brennan et al.
2023/0049924 A1 2/2023 Johannes et al.
2023/0052238 A1 2/2023 Oluwasogo
2023/0062994 A1 3/2023 Ecklund et al.
2023/0070347 A1 3/2023 Watson et al.
2023/0073708 A1 3/2023 Xu et al.
2023/0089032 A1 3/2023 Hughett et al.
2023/0091118 A1 3/2023 Watson
2023/0099821 A1 3/2023 Radl et al.
2023/0099991 A1 3/2023 Bianchi et al.
2023/0105001 A1 4/2023 Whittome et al.
2023/0110577 A1 4/2023 Choi
2023/0138269 A1 5/2023 Abdelal et al.
2023/0145365 A1 5/2023 Martin et al.
2023/0155253 A1 5/2023 Yin et al.
2023/0210504 A1 7/2023 Kuroda et al.
2023/0210685 A1 7/2023 Fallows et al.
2023/0218426 A1 7/2023 Hughett
2023/0240884 A1 8/2023 Davis et al.
2023/0248562 A1 8/2023 Sanchez et al.
2023/0248564 A1 8/2023 Mann et al.
2023/0255812 A1 8/2023 Sanchez et al.
2023/0255813 A1 8/2023 Sanchez et al.
2023/0255815 A1 8/2023 Newton
2023/0263650 A1 8/2023 Sanchez et al.
2023/0263655 A1 8/2023 Johannes et al.
2023/0277360 A1 9/2023 Lambert et al.
2023/0277362 A1 9/2023 Davis et al.
2023/0285178 A1 9/2023 Sanchez et al.
2023/0293339 A1 9/2023 James
2023/0301846 A1 9/2023 Greenwood
2023/0355423 A1 11/2023 Stevenson et al.
2023/0404791 A1 12/2023 Ecklund et al.
2024/0008444 A1 1/2024 Su et al.
2024/0009023 A1 1/2024 Johannes et al.
2024/0024170 A1 1/2024 Scott
2024/0033148 A1 2/2024 Gordon et al.
2024/0041638 A1 2/2024 Johannes et al.
2024/0058160 A1 2/2024 Young Joyner et al.
2024/0058161 A1 2/2024 Ulreich et al.
2024/0058520 A1 2/2024 Yin et al.
2024/0065881 A1 2/2024 Kuroda et al.
2024/0082044 A1 3/2024 Nguyen et al.
2024/0099874 A1 3/2024 Sanchez et al.
2024/0108268 A1 4/2024 Woodard et al.
2024/0110318 A1 4/2024 Bendt et al.
2024/0122773 A1 4/2024 Nguyen et al.
2024/0123134 A1 4/2024 Kharkar et al.
2024/0148539 A1 5/2024 Austermann et al.
2024/0156633 A1 5/2024 Fallows et al.
2024/0252343 A1 8/2024 Voda
2024/0261131 A1 8/2024 Garvey et al.
2024/0268986 A1 8/2024 Barnes et al.
2024/0268989 A1 8/2024 Martin et al.
2024/0269027 A1 8/2024 Tourchak et al.
2024/0285425 A1 8/2024 Donohoe et al.
2024/0325190 A1 10/2024 Minchew et al.
2024/0358539 A1 10/2024 Gallup
2024/0358542 A1 10/2024 Richardson et al.
2024/0374414 A1 11/2024 Richardson et al.
2025/0009552 A1 1/2025 Blabas et al.
2025/0073055 A1 3/2025 Ecklund et al.
2025/0107920 A1 4/2025 Fallows et al.
2025/0107921 A1 4/2025 Sanchez et al.

FOREIGN PATENT DOCUMENTS

AU 2022349367 A1 4/2024
CA 2165286 C 9/1999
CA 2354132 A1 6/2000
CA 2359091 C 9/2003
CA 2488867 C 8/2007
CA 3050918 A1 8/2018
CA 3098571 A1 11/2019
CA 3188651 A1 7/2023
CN 2269203 Y 12/1997
CN 1332620 A 1/2002
CN 1434693 A 8/2003
CN 1533755 A 10/2004
CN 1602825 A 4/2005
CN 1720888 A 1/2006
CN 2936204 Y 8/2007
CN 101262836 A 9/2008
CN 101522148 A 9/2009
CN 102159159 A 8/2011
CN 202184840 U 4/2012
CN 102481441 A 5/2012
CN 202463712 U 10/2012
CN 202950810 U 5/2013
CN 103533968 A 1/2014
CN 103717180 A 4/2014
CN 204562697 U 8/2015
CN 105411783 A 3/2016
CN 105451693 A 3/2016
CN 105534632 A 5/2016
CN 106132360 A 11/2016
CN 205849719 U 1/2017
CN 205924282 U 2/2017

(56) References Cited

FOREIGN PATENT DOCUMENTS

| | | | |
|---|---|---|---|
| CN | 106726089 | A | 5/2017 |
| CN | 107847384 | A | 3/2018 |
| CN | 107920912 | A | 4/2018 |
| CN | 108420590 | A | 8/2018 |
| CN | 209285902 | U | 8/2019 |
| CN | 110381883 | A | 10/2019 |
| CN | 211198839 | U | 8/2020 |
| CN | 111991136 | A | 11/2020 |
| CN | 112022488 | A | 12/2020 |
| CN | 212234893 | U | 12/2020 |
| CN | 212466312 | U | 2/2021 |
| CN | 112566550 | A | 3/2021 |
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |
| DE | 79818 | C | 10/1893 |
| DE | 1516466 | A1 | 6/1969 |
| DE | 2721330 | A1 | 11/1977 |
| DE | 2742298 | A1 | 3/1978 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 102005037762 | B3 | 9/2006 |
| DE | 102011103783 | A1 | 12/2012 |
| DE | 102012112818 | A1 | 6/2014 |
| DE | 202015104597 | U1 | 7/2016 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0220962 | A1 | 5/1987 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0483730 | A1 | 5/1992 |
| EP | 0610638 | A1 | 8/1994 |
| EP | 0613355 | A1 | 9/1994 |
| EP | 0613355 | B1 | 1/1997 |
| EP | 0787472 | A1 | 8/1997 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3569205 | B1 | 6/2023 |
| EP | 4382082 | A2 | 6/2024 |
| EP | 4445881 | A2 | 10/2024 |
| EP | 4464288 | A2 | 11/2024 |
| EP | 4527361 | A2 | 3/2025 |
| FR | 2826704 | A1 | 1/2003 |
| GB | 871820 | A | 7/1961 |
| GB | 873045 | A | 7/1961 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58188016 | U | 12/1983 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H05123349 | A | 5/1993 |
| JP | H05123350 | A | 5/1993 |
| JP | H0626264 | U | 4/1994 |
| JP | 3087938 | B2 | 10/1995 |
| JP | H085630 | A | 1/1996 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003528691 | A | 9/2003 |
| JP | 2004057578 | A | 2/2004 |
| JP | 2004130056 | A | 4/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |

(56) References Cited

FOREIGN PATENT DOCUMENTS

| | | | |
|---|---|---|---|
| JP | 2007259898 | A | 10/2007 |
| JP | 4039641 | B2 | 11/2007 |
| JP | 2008005975 | A | 1/2008 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011218130 | A | 11/2011 |
| JP | 2011224070 | A | 11/2011 |
| JP | 3175719 | U | 4/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 2017070400 | A | 4/2017 |
| JP | 2017512603 | A | 5/2017 |
| JP | 2017201272 | A | 11/2017 |
| JP | 2019010375 | A | 1/2019 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020520775 | A | 7/2020 |
| JP | 2021007472 | A | 1/2021 |
| JP | 2021120686 | A | 8/2021 |
| JP | 2021522009 | A | 8/2021 |
| JP | 2021522013 | A | 8/2021 |
| JP | 7129493 | B2 | 8/2022 |
| JP | 2023532132 | A | 7/2023 |
| KR | 200290061 | Y1 | 9/2002 |
| KR | 20030047451 | A | 6/2003 |
| KR | 20080005516 | A | 1/2008 |
| KR | 20090072069 | A | 7/2009 |
| KR | 20090104426 | A | 10/2009 |
| KR | 20090110359 | A | 10/2009 |
| KR | 20120005922 | A | 1/2012 |
| KR | 20140039485 | A | 4/2014 |
| KR | 101432639 | B1 | 8/2014 |
| KR | 20180106659 | A | 10/2018 |
| KR | 20180108774 | A | 10/2018 |
| KR | 20230034343 | A | 3/2023 |
| PT | 2068717 | E | 6/2013 |
| SE | 505542 | C2 | 9/1997 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9303690 | A1 | 3/1993 |
| WO | 9307839 | A1 | 4/1993 |
| WO | 9309736 | A2 | 5/1993 |
| WO | 9309736 | A3 | 6/1993 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |

| | | | |
|---|---|---|---|
| WO | 0033773 | A1 | 6/2000 |
| WO | 0057784 | A1 | 10/2000 |
| WO | 0069377 | A1 | 11/2000 |
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005051252 | A1 | 6/2005 |
| WO | 2005060558 | A2 | 7/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007134608 | A2 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012020506 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |

(56) References Cited

FOREIGN PATENT DOCUMENTS

| | | | |
|---|---|---|---|
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018235026 | A1 | 12/2018 |
| WO | 2018235065 | A1 | 12/2018 |
| WO | 2019004404 | A1 | 1/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020033752 | A1 | 2/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016056 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150290 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022173803 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2022251184 | A1 | 12/2022 |
| WO | 2022251425 | A1 | 12/2022 |
| WO | 2022271783 | A1 | 12/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023018656 | A1 | 2/2023 |
| WO | 2023018657 | A1 | 2/2023 |
| WO | 2023023777 | A1 | 3/2023 |
| WO | 2023034139 | A1 | 3/2023 |

(56) References Cited

FOREIGN PATENT DOCUMENTS

| | | | |
|---|---|---|---|
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049156 | A1 | 3/2023 |
| WO | 2023049175 | A1 | 3/2023 |
| WO | 2023086394 | A1 | 5/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023163725 | A1 | 8/2023 |
| WO | 2023191764 | A1 | 10/2023 |
| WO | 2023244238 | A1 | 12/2023 |
| WO | 2024043871 | A1 | 2/2024 |
| WO | 2024058788 | A1 | 3/2024 |
| WO | 2024253655 | A1 | 12/2024 |
| WO | 2025034959 | A1 | 2/2025 |
| WO | 2025038087 | A1 | 2/2025 |
| WO | 2025038088 | A1 | 2/2025 |
| WO | 2025071622 | A1 | 4/2025 |

OTHER PUBLICATIONS

Non-Final Office Action for U.S. Appl. No. 14/592,591 mailed Mar. 20, 2020.
Non-Final Office Action for U.S. Appl. No. 16/905,400 mailed Apr. 27, 2022.
U.S. Appl. No. 17/661,090, filed Apr. 28, 2022.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Feb. 16, 2022.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/452,145 mailed Mar. 25, 2022.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.

(56) References Cited

OTHER PUBLICATIONS

International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 21, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.

(56) References Cited

OTHER PUBLICATIONS

Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/899,956 mailed Apr. 19, 2022.
Notice of Allowance for U.S. Appl. No. 16/899,956 mailed Dec. 29, 2021.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/384,196, filed Dec. 19, 2016.
U.S. Appl. No. 15/611,587, filed Jun. 1, 2017.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/754,736, filed Apr. 11, 2022.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,977, filed Jan. 30, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.

(56) References Cited

OTHER PUBLICATIONS

U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology 2005-06", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.

(56) References Cited

OTHER PUBLICATIONS

"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister, "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.
Jagota , et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee , et al., "Continuous Fabrication of Wide-Tip Microstructures for Bio-Inspired Dry Adhesives via Tip Inking Process", Journal of Chemistry, Jan. 2, 2019, pp. 1-5.
Macaulay , et al., "A Noninvasive Continence Management System: Development and Evaluation of a Novel Toileting Device for Women", The Wound, Ostomy and Continence Nurses Society, 2007, pp. 641-648.
Newman , et al., "The Urinary Incontinence Sourcebook", Petition for Interparties Review, 1997, 23 pages.
Newton , et al., "Measuring Safety, Effectiveness and Ease of Use of PureWick in the Management of Urinary Incontinence in Bedbound Women: Case Studies", Jan. 8, 2016, 11 pages.
Parmar , "10 Finalists Chosen for Dare-to-Dream Medtech Design Challenge (PureWick)", Design Services, Nov. 10, 2014, 3 pages.
Parness , et al., "A microfabricated wedge-shaped adhesive array displaying gecko-like dynamic adhesion, directionality", J.R. Soc. Interface, 2009, pp. 1223-1232.
Purewick , "Incontinence Relief for Women", Presentation, Sep. 23, 2015, 7 pages.
Pytlik , "Super Absorbent Polymers", University of Buffalo.
Sachtman , "New Relief for Pilots? It Depends", Wired, 2008, 2 pages.
Tsipenyuk , et al., "Use of biomimetic hexagonal surface texture in friction against lubricated skin", Journal of The Royal Society—Interface, 2014, pp. 1-6.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 16/904,868 mailed Jun. 15, 2022.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/662,700 mailed Jan. 30, 2023.
Corrected Notice of Allowability for U.S. Appl. No. 16/369,676 mailed Dec. 7, 2023.
Final Office Action for U.S. Appl. No. 16/245,726 mailed Nov. 25, 2022.
Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 10, 2023.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/478,180 mailed May 31, 2023.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.

(56) References Cited

OTHER PUBLICATIONS

Final Office Action for U.S. Appl. No. 17/179,116 mailed Oct. 31, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/662,700 mailed Sep. 30, 2022.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 18/139,523 mailed Dec. 22, 2023.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/IB2021/057173 mailed Nov. 5, 2021.
International Search Report and Written Opinion from International Application No. PCT/US2021/039866 mailed Oct. 7, 2021.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.

(56) References Cited

OTHER PUBLICATIONS

International Search Report and Written Opinion from International Application No. PCT/US2023/018474 mailed Sep. 11, 2023.
International Search Report and Written Opinion from International Application No. PCT/US2023/024805 mailed Dec. 14, 2023.
Issue Notification for U.S. Appl. No. 16/245,726 mailed Oct. 18, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 17/461,036 mailed Oct. 11, 2023.
Issue Notification for U.S. Appl. No. 17/663,046 mailed Dec. 20, 2023.
Non-Final Office Action for U.S. Appl. No. 16/433,773 mailed Apr. 11, 2023.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,258 mailed Apr. 26, 2023.
Non-Final Office Action for U.S. Appl. No. 16/478,180 mailed Dec. 20, 2022.
Non-Final Office Action for U.S. Appl. No. 16/478,180 mailed Nov. 7, 2023.
Non-Final Office Action for U.S. Appl. No. 16/904,868 mailed Mar. 15, 2023.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,585 mailed Mar. 29, 2023.
Non-Final Office Action for U.S. Appl. No. 17/051,600 mailed Jan. 17, 2024.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/444,792 mailed Nov. 17, 2023.
Non-Final Office Action for U.S. Appl. No. 17/446,256 mailed Apr. 13, 2023.
Non-Final Office Action for U.S. Appl. No. 17/446,654 mailed Sep. 8, 2023.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,345 mailed Jan. 17, 2024.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/453,560 mailed Oct. 16, 2023.
Non-Final Office Action for U.S. Appl. No. 17/501,591 mailed Apr. 25, 2023.
Non-Final Office Action for U.S. Appl. No. 17/645,821 mailed Oct. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/653,137 mailed Jan. 18, 2024.
Non-Final Office Action for U.S. Appl. No. 17/655,464 mailed Mar. 14, 2023.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/662,700 mailed Jul. 22, 2022.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 17/808,354 mailed Nov. 28, 2023.
Non-Final Office Action for U.S. Appl. No. 18/134,857 mailed Jan. 25, 2024.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 18/198,464 mailed Dec. 7, 2023.
Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 16/449,039 mailed Dec. 15, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/905,400 mailed Aug. 17, 2022.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/326,980 mailed Jan. 29, 2024.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/662,700 mailed Nov. 15, 2023.

(56) References Cited

OTHER PUBLICATIONS

Notice of Allowance for U.S. Appl. No. 17/663,046 mailed Jan. 30, 2023.
Notice of Allowance for U.S. Appl. No. 18/299,788 mailed Jul. 24, 2023.
Notice of Allowance for U.S. Appl. No. 18/299,788 mailed Nov. 6, 2023.
Notice of Allowance for U.S. Appl. No. 29/741,751 mailed Jun. 9, 2022.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 18/134,857 mailed Oct. 23, 2023.
Text Messages to Lorena Eckert Re Prototype PureWick Holder dated Apr. 16, 2022.
U.S. Appl. No. 17/451,719, filed Oct. 19, 2021.
U.S. Appl. No. 17/662,700, filed May 10, 2022.
U.S. Appl. No. 17/663,046, filed May 12, 2022.
U.S. Appl. No. 17/664,487, filed May 23, 2022.
U.S. Appl. No. 17/664,914, filed May 25, 2022.
U.S. Appl. No. 17/749,340, filed May 20, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 62/967,158, filed Jan. 26, 2020.
U.S. Appl. No. 62/991,754, filed Mar. 19, 2020.
U.S. Appl. No. 63/008,112, filed Apr. 10, 2020.
U.S. Appl. No. 63/150,640, filed Feb. 18, 2021.
U.S. Appl. No. 63/191,558, filed May 21, 2021.
U.S. Appl. No. 63/192,289, filed May 24, 2021.
U.S. Appl. No. 63/241,328, filed Sep. 7, 2021.
U.S. Appl. No. 63/308,190, filed Feb. 9, 2022.
U.S. Appl. No. 63/596,012, filed Nov. 3, 2023.
U.S. Appl. No. 63/608,553, filed Dec. 11, 2023.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020 , Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Merriam-Webster Dictionary, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, Mar./Apr. 1993, pp. 51-55.
Vinas, "A Solution for an Awkward—But Serious—Subject", http://www.aero-news.net/index.cfm?do=main.textpost&id=69ae2bb1-838b-4098-a7b5-7flbb2505688 last accessed Feb. 8, 2021.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/051,585 mailed Oct. 8, 2024.
Advisory Action for U.S. Appl. No. 17/444,792 mailed Jul. 8, 2024.
Advisory Action for U.S. Appl. No. 17/446,256 mailed Nov. 19, 2024.
Advisory Action for U.S. Appl. No. 17/446,654 mailed Apr. 15, 2024.
Advisory Action for U.S. Appl. No. 17/446,654 mailed Feb. 28, 2025.
Advisory Action for U.S. Appl. No. 17/450,864 mailed Mar. 21, 2024.
Advisory Action for U.S. Appl. No. 17/451,345 mailed Jul. 3, 2024.

(56) References Cited

OTHER PUBLICATIONS

Advisory Action for U.S. Appl. No. 17/501,591 mailed Feb. 22, 2024.
Advisory Action for U.S. Appl. No. 17/597,673 mailed Jan. 7, 2025.
Advisory Action for U.S. Appl. No. 17/645,821 mailed Jul. 2, 2024.
Advisory Action for U.S. Appl. No. 17/646,771 mailed Feb. 29, 2024.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 17/655,464 mailed Feb. 25, 2025.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/003,029 mailed Jan. 8, 2025.
Advisory Action for U.S. Appl. No. 18/134,857 mailed Oct. 23, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Advisory Action for U.S. Appl. No. 18/164,800 mailed Jan. 8, 2025.
Communication of Notice of Opposition of European Application No. 17807547.9 mailed Jan. 5, 2024.
Corrected Notice of Allowability for U.S. Appl. No. 17/326,980 mailed Feb. 8, 2024.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/646,771 mailed Jan. 17, 2025.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/452,258 mailed Jan. 6, 2025.
Final Office Action for U.S. Appl. No. 16/478,180 mailed Feb. 28, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/451,345 mailed Feb. 6, 2025.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/597,673 mailed Oct. 22, 2024.
Final Office Action for U.S. Appl. No. 17/625,941 mailed Feb. 18, 2025.
Final Office Action for U.S. Appl. No. 17/645,821 mailed Apr. 3, 2024.
Final Office Action for U.S. Appl. No. 17/653,137 mailed Aug. 7, 2024.
Final Office Action for U.S. Appl. No. 17/653,314 mailed Jan. 30, 2025.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 17/808,354 mailed Apr. 10, 2024.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/140,163 mailed Mar. 27, 2024.
Final Office Action for U.S. Appl. No. 18/164,800 mailed Oct. 22, 2024.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031432 mailed Feb. 29, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
International Search Report and Written Opinion from International Application No. PCT/US2024/053681 mailed Jan. 27, 2025.
Issue Notification for U.S. Appl. No. 16/369,676 mailed Oct. 2, 2024.
Issue Notification for U.S. Appl. No. 16/449,039 mailed Jun. 19, 2024.
Issue Notification for U.S. Appl. No. 16/452,145 mailed Oct. 23, 2024.
Issue Notification for U.S. Appl. No. 16/478,180 mailed Mar. 5, 2025.

(56) References Cited

OTHER PUBLICATIONS

Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/179,116 mailed Dec. 25, 2024.
Issue Notification for U.S. Appl. No. 17/326,980 mailed Jul. 10, 2024.
Issue Notification for U.S. Appl. No. 17/447,123 mailed Nov. 13, 2024.
Issue Notification for U.S. Appl. No. 17/448,811 mailed Jul. 3, 2024.
Issue Notification for U.S. Appl. No. 17/450,864 mailed Jan. 8, 2025.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/633,330 mailed Feb. 26, 2025.
Issue Notification for U.S. Appl. No. 17/657,474 mailed Jun. 19, 2024.
Issue Notification for U.S. Appl. No. 17/661,090 mailed Feb. 5, 2025.
Issue Notification for U.S. Appl. No. 17/662,700 mailed Oct. 23, 2024.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/140,751 mailed Feb. 12, 2025.
Issue Notification for U.S. Appl. No. 18/198,464 mailed Nov. 20, 2024.
Issue Notification for U.S. Appl. No. 18/299,788 mailed Feb. 21, 2024.
Issue Notification for U.S. Appl. No. 18/389,009 mailed Dec. 18, 2024.
Issue Notification for U.S. Appl. No. 18/426,795 mailed Feb. 19, 2025.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/433,773 mailed Feb. 28, 2025.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 16/904,868 mailed Mar. 12, 2024.
Non-Final Office Action for U.S. Appl. No. 17/051,600 mailed Feb. 28, 2025.
Non-Final Office Action for U.S. Appl. No. 17/179,116 mailed Feb. 26, 2024.
Non-Final Office Action for U.S. Appl. No. 17/378,015 mailed Jul. 5, 2024.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/446,256 mailed Feb. 13, 2024.
Non-Final Office Action for U.S. Appl. No. 17/446,654 mailed Jun. 25, 2024.
Non-Final Office Action for U.S. Appl. No. 17/450,864 mailed May 29, 2024.
Non-Final Office Action for U.S. Appl. No. 17/451,345 mailed Jul. 25, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/597,673 mailed Mar. 20, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/646,771 mailed Apr. 24, 2024.
Non-Final Office Action for U.S. Appl. No. 17/653,137 mailed Jan. 28, 2025.
Non-Final Office Action for U.S. Appl. No. 17/653,314 mailed Aug. 29, 2024.
Non-Final Office Action for U.S. Appl. No. 17/653,920 mailed Mar. 15, 2024.
Non-Final Office Action for U.S. Appl. No. 17/653,920 mailed Nov. 27, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/664,914 mailed Jan. 31, 2024.
Non-Final Office Action for U.S. Appl. No. 17/749,340 mailed Aug. 14, 2024.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/809,083 mailed Mar. 7, 2025.
Non-Final Office Action for U.S. Appl. No. 17/907,125 mailed Dec. 13, 2024.
Non-Final Office Action for U.S. Appl. No. 17/996,064 mailed Mar. 6, 2025.
Non-Final Office Action for U.S. Appl. No. 18/003,029 mailed Mar. 26, 2024.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/389,009 mailed May 24, 2024.
Non-Final Office Action for U.S. Appl. No. 18/426,795 mailed Aug. 9, 2024.

(56) References Cited

OTHER PUBLICATIONS

Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 16/904,868 mailed Sep. 29, 2024.
Notice of Allowance for U.S. Appl. No. 17/051,550 mailed Feb. 7, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/326,980 mailed Apr. 5, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/596,629 mailed Jan. 29, 2025.
Notice of Allowance for U.S. Appl. No. 17/597,673 mailed Feb. 26, 2025.
Notice of Allowance for U.S. Appl. No. 17/646,771 mailed Dec. 17, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/661,090 mailed Oct. 30, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 17/749,340 mailed Feb. 14, 2025.
Notice of Allowance for U.S. Appl. No. 17/996,155 mailed Mar. 11, 2025.
Notice of Allowance for U.S. Appl. No. 18/134,857 mailed Feb. 20, 2025.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Apr. 17, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/667,097 mailed Mar. 20, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
Restriction Requirement for U.S. Appl. No. 17/929,887 mailed Mar. 10, 2025.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/013,822, filed Sep. 7, 2020.
U.S. Appl. No. 17/444,792, filed Aug. 10, 2021.
U.S. Appl. No. 18/249,577, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.

(56) References Cited

OTHER PUBLICATIONS

U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/103,165, filed Feb. 11, 2025.
U.S. Appl. No. 63/564,696, filed Mar. 13, 2024.
U.S. Appl. No. 63/181,709, filed Apr. 29, 2021.
U.S. Appl. No. 63/561,893, filed Dec. 11, 2023.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Wikipedia article, "Decibel", https://web.archive.org/web/20200415219l7/https://en.wikipedia/org/wiki/Decibel last accessed Mar. 11, 2024, 21 pages.
Wikipedia article, "Fiberglass". https://web.archive.org.web/20200309194847/https://en.wikipedia.org/wiki/Fiberglass last accessed Mar. 11, 2024.
Wikipedia article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 16/452,258 mailed May 5, 2025.
Advisory Action for U.S. Appl. No. 17/451,345 mailed May 13, 2025.
Advisory Action for U.S. Appl. No. 17/595,747 mailed Mar. 17, 2025.
Advisory Action for U.S. Appl. No. 17/653,314 mailed Apr. 8, 2025.
Advisory Action for U.S. Appl. No. 17/664,487 mailed Apr. 24, 2025.
Corrected Notice of Allowability for U.S. Appl. No. 17/996,253 mailed Apr. 28, 2025.
Corrected Notice of Allowability for U.S. Appl. No. 18/134,857 mailed Mar. 14, 2025.
Final Office Action for U.S. Appl. No. 17/378,015 mailed Jun. 18, 2025.
Final Office Action for U.S. Appl. No. 17/446,256 mailed Jun. 11, 2025.
Final Office Action for U.S. Appl. No. 17/597,408 mailed Mar. 24, 2025.
Final Office Action for U.S. Appl. No. 17/614,173 mailed May 20, 2025.
Final Office Action for U.S. Appl. No. 17/628,411 mailed Apr. 30, 2025.
Final Office Action for U.S. Appl. No. 17/653,920 mailed Apr. 24, 2025.
Final Office Action for U.S. Appl. No. 17/757,311 mailed Mar. 31, 2025.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/907,125 mailed Apr. 30, 2025.
Final Office Action for U.S. Appl. No. 18/139,523 mailed May 8, 2025.
International Search Report and Written Opinion from International Application No. PCT/US2023/036875 mailed May 31, 2024.
International Search Report and Written Opinion from International Application No. PCT/US2023/077205 mailed Jul. 19, 2024.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
Issue Notification for U.S. Appl. No. 16/904,868 mailed Apr. 30, 2025.
Issue Notification for U.S. Appl. No. 17/051,585 mailed Mar. 26, 2025.
Issue Notification for U.S. Appl. No. 17/597,673 mailed Jun. 4, 2025.
Issue Notification for U.S. Appl. No. 17/646,771 mailed Mar. 19, 2025.
Issue Notification for U.S. Appl. No. 17/749,340 mailed May 28, 2025.
Issue Notification for U.S. Appl. No. 18/134,857 mailed May 28, 2025.
Issue Notification for U.S. Appl. No. 18/415,080 mailed Apr. 9, 2025.
Issue Notification for U.S. Appl. No. 18/584,002 mailed Apr. 16, 2025.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/446,654 mailed May 1, 2025.
Non-Final Office Action for U.S. Appl. No. 17/451,354 mailed Mar. 19, 2025.
Non-Final Office Action for U.S. Appl. No. 17/595,747 mailed Jun. 12, 2025.
Non-Final Office Action for U.S. Appl. No. 17/631,619 mailed Mar. 19, 2025.
Non-Final Office Action for U.S. Appl. No. 17/645,821 mailed Mar. 31, 2025.
Non-Final Office Action for U.S. Appl. No. 17/653,314 mailed May 8, 2025.
Non-Final Office Action for U.S. Appl. No. 17/655,464 mailed Mar. 20, 2025.
Non-Final Office Action for U.S. Appl. No. 17/664,487 mailed May 19, 2025.
Non-Final Office Action for U.S. Appl. No. 17/754,736 mailed Mar. 31, 2025.
Non-Final Office Action for U.S. Appl. No. 17/756,201 mailed Apr. 24, 2025.
Non-Final Office Action for U.S. Appl. No. 17/758,152 mailed Apr. 8, 2025.
Non-Final Office Action for U.S. Appl. No. 17/809,083 mailed Apr. 2, 2025.
Non-Final Office Action for U.S. Appl. No. 17/878,268 mailed Mar. 17, 2025.
Non-Final Office Action for U.S. Appl. No. 17/912,147 mailed May 29, 2025.
Non-Final Office Action for U.S. Appl. No. 18/003,029 mailed Apr. 18, 2025.
Non-Final Office Action for U.S. Appl. No. 18/006,807 mailed May 29, 2025.
Non-Final Office Action for U.S. Appl. No. 18/042,842 mailed May 22, 2025.

(56) References Cited

OTHER PUBLICATIONS

Non-Final Office Action for U.S. Appl. No. 18/043,618 mailed May 19, 2025.
Non-Final Office Action for U.S. Appl. No. 18/164,800 mailed Apr. 25, 2025.
Non-Final Office Action for U.S. Appl. No. 18/247,986 mailed Jun. 4, 2025.
Non-Final Office Action for U.S. Appl. No. 18/264,004 mailed May 15, 2025.
Notice of Allowance for U.S. Appl. No. 17/444,792 mailed Mar. 28, 2025.
Notice of Allowance for U.S. Appl. No. 17/596,629 mailed May 27, 2025.
Notice of Allowance for U.S. Appl. No. 17/758,316 mailed Mar. 24, 2025.
Notice of Allowance for U.S. Appl. No. 17/996,253 mailed Apr. 11, 2025.
Notice of Allowance for U.S. Appl. No. 17/996,468 mailed Apr. 14, 2025.
Notice of Allowance for U.S. Appl. No. 18/007,105 mailed Jun. 17, 2025.
Restriction Requirement for U.S. Appl. No. 17/930,238 mailed Apr. 17, 2025.
Restriction Requirement for U.S. Appl. No. 18/041,109 mailed Jun. 4, 2025.
Restriction Requirement for U.S. Appl. No. 18/150,360 mailed May 19, 2025.
Supplemental Notice of Allowance for U.S. Appl. No. 17/597,673 mailed Apr. 10, 2025.
U.S. Appl. No. 17/596,629, filed Dec. 15, 2021.
U.S. Appl. No. 19/078,602, filed Mar. 13, 2025.
U.S. Appl. No. 19/092,262, filed Mar. 27, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.

* cited by examiner

FLUID COLLECTION ASSEMBLIES INCLUDING A SAMPLE PORT

CROSS-REFERENCE TO RELATED APPLICATIONS

This application is a U.S. Nationalization of PCT International Application No. PCT/US2020/057562, filed on Oct. 27, 2020, which claims priority to U.S. Provisional Application No. 62/926,767 filed on Oct. 28, 2019, the disclosures of each of which is incorporated herein, in its entirety, by this reference.

BACKGROUND

A person or animal may have limited or impaired mobility such that typical urination processes are challenging or impossible. For example, a person may experience or have a disability that impairs mobility. A person may have restricted travel conditions such as those experienced by pilots, drivers, and workers in hazardous areas. Additionally, sometimes urine collection is needed for monitoring purposes or clinical testing.

Urinary catheters, such as a Foley catheter, can be used to address some of these circumstances, such as incontinence. Unfortunately, urinary catheters can be uncomfortable, painful, and can lead to complications, such as infections. Further, obtaining samples from urinary catheters, under certain circumstances, may be challenging or difficult under certain circumstances.

SUMMARY

In an embodiment, a fluid collection assembly is disclosed. The fluid collection assembly includes a fluid impermeable barrier including a first end region and a second end region longitudinally spaced from the first end. The fluid impermeable barrier includes a sump that forms at least a portion of the first end region. The fluid impermeable barrier defines at least one opening, a chamber in fluid communication with the at least one opening, a fluid reservoir defined by at least a portion of the sump, and a fluid outlet in fluid communication with the fluid reservoir. The fluid collection assembly also includes at least one wicking material disposed in the fluid impermeable barrier. Further, the fluid collection assembly includes a sample port attached to the sump and in fluid communication with the fluid reservoir. The sample port is configured to switch between a closed state that restricts fluid flow through the sample port and an open state that permits fluid flow through the sample port. The sample port is configured to be connected to a fluid collector.

In an embodiment, a fluid collection system is disclosed. The fluid collection system includes a fluid collection assembly and a fluid collector. The fluid collection assembly includes a fluid impermeable barrier including a first end region and a second end region longitudinally spaced from the first end. The fluid impermeable barrier includes a sump that forms at least a portion of the first end region. The fluid impermeable barrier defines at least one opening, a chamber in fluid communication with the at least one opening, a fluid reservoir defined by at least a portion of the sump, and a fluid outlet in fluid communication with the fluid reservoir. The fluid collection assembly also includes at least one wicking material disposed in the fluid impermeable barrier. Further, the fluid collection assembly includes a sample port attached to the sump and in fluid communication with the fluid reservoir. The sample port is configured to switch between a closed state that restricts fluid flow through the sample port and an open state that permits fluid flow through the sample port. The sample port is configured to be connected to a fluid collector.

In an embodiment, a method of using a fluid collection system is disclosed. The method includes attaching the fluid collector to the sample port. The method also includes receiving bodily fluids from an individual through the at least one opening, into the chamber, and to the fluid reservoir. The method further includes removing at least some of the bodily fluids that are present in the fluid reservoir with the fluid collector. Additionally, the method includes detaching the fluid collector from the sample port. Further, the method includes switching the sample port from the open state to the closed state. The method additionally includes removing substantially all of a remainder of the bodily fluids present in the fluid reservoir through the fluid outlet using a suction three.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
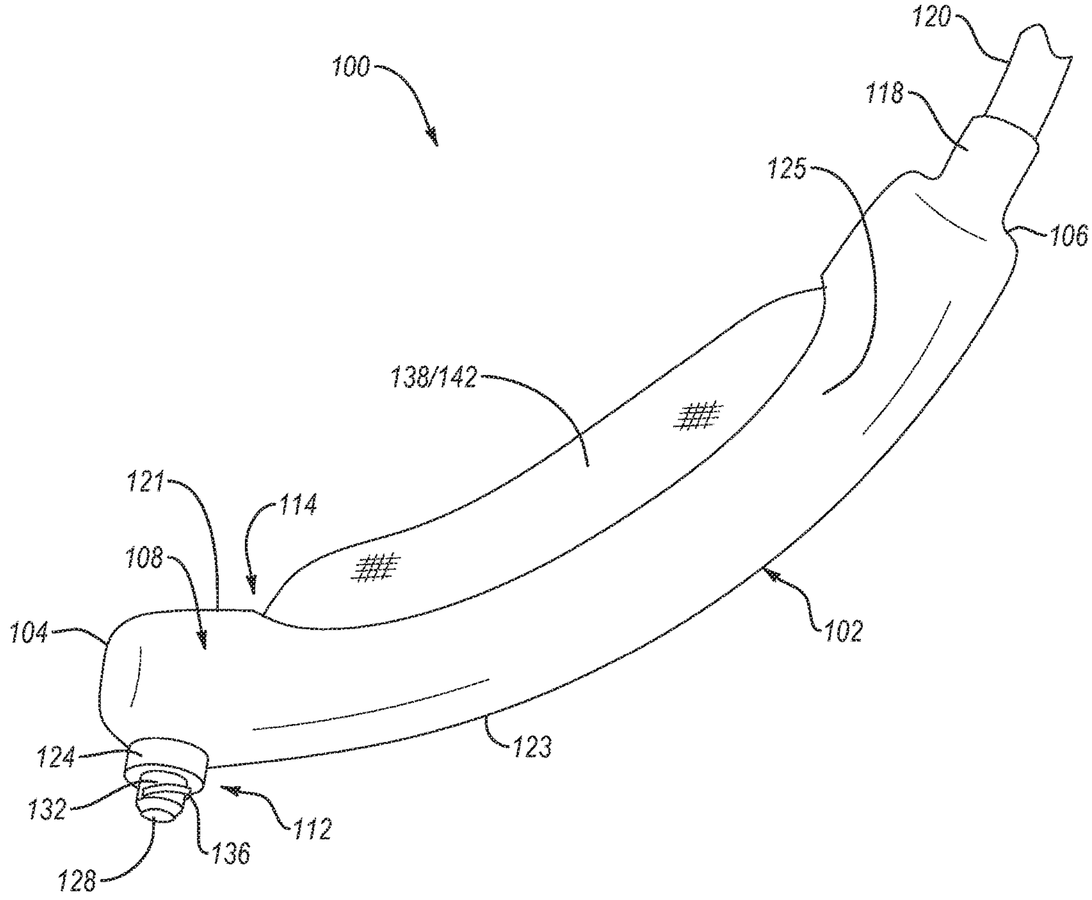
FIG. 1A is a schematic isometric view of a fluid collection assembly, according to an embodiment.

Fluid collection assemblies including a sample port, systems including the same, and methods of using the same are disclosed herein. An example fluid collection assembly includes a fluid impermeable barrier including a first end region, a second end region opposite the first end region, and a sump that forms at least a portion of the first end region. The fluid impermeable barrier also defines at least one opening between the first end region and the second end region and a fluid reservoir that is defined by at least a portion of the sump. The fluid collection assembly also includes at least one wicking material disposed in the chamber and a sample port extending from the sump. The sample port is configured to be connected to a fluid collector (e.g., a syringe or a vial). The sample port is in fluid communication with the fluid reservoir such that a sample of the bodily fluids (e.g., urine) received by the fluid collection assembly may be obtained.

During use, the opening of the fluid impermeable barrier is positioned adjacent to the urethral opening of an individual. Bodily fluids (e.g., urine) that are emitted from the urethral opening are received by the wicking material through the opening and flow through the wicking material to the fluid reservoir. The bodily fluids are removed from the fluid reservoir using a suction force.

With conventional catheters (e.g., Foley catheters), sample ports are provided on a tube extending between the urethral opening and a drainage bag. Samples may be obtained from these sample ports by connecting a fluid collector to the port. The fluid collector then removes a sample of the bodily fluids by pulling the bodily fluids flowing in the tube or by kinking the tube followed by collecting the pooled bodily fluids. However, such methods of obtaining samples from the fluid collection assemblies according to any of the embodiments of the present disclosure (e.g., fluid collection assemblies 100, 200, 300*a*, 300*b*, 400*a*, 400*b*, 400*c*, 500 and 600 shown in FIGS. 1A-6) can be difficult and/or impossible for at least one of several reasons. For example, the fluid collection assemblies according to any of the embodiments of the present disclosure remove the bodily fluids from the fluid reservoir by applying a vacuum force from a tube. The suction force tends to move the fluid through the tube at relatively high velocities which makes removing of the bodily fluids flowing in the tube difficult. Further, kinking the tube to pool the bodily fluids does not cause the bodily fluids to pool in the tube since kinking the tube stops the suction force that pulls the bodily fluids into the tube.

The samples ports according to any embodiments of the present disclosure remedy at least some of the problems associated with obtaining samples of the bodily fluids using conventional sample ports. For example, the sample ports according to any of the embodiments of the present disclosure extend from the sump of the fluid reservoir instead of located on a portion of the tube. The bodily fluids that are present in the fluid reservoir tend to flow at lower velocities (e.g., are more stationary) that the bodily fluids that flow through the tube. Further, the bodily fluids flow towards the fluid reservoir even in the absence of the suction force since, for example, the fluid reservoir is the gravimetric low point of the fluid collection assembly. As such, the suction force that removes the bodily fluids from the fluid reservoir may be stopped (e.g., the tube is kinked) thereby causing the bodily fluids to pool in the fluid reservoir.

Figure 1B:
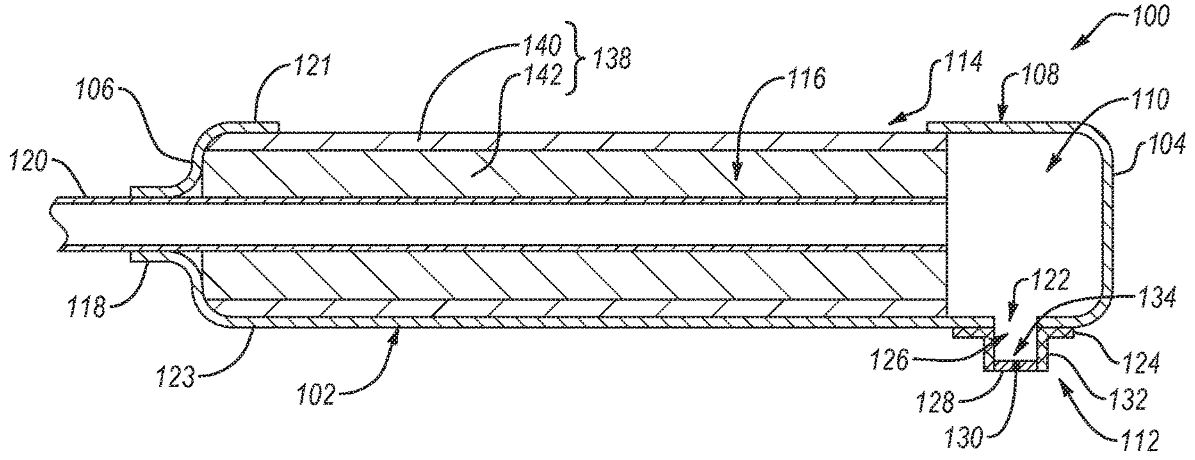
FIG. 1B is a cross-sectional view of the fluid collection assembly, according to an embodiment.

FIG. 1A is a schematic isometric view of a fluid collection assembly 100, according to an embodiment. FIG. 1B is a cross-sectional view of the fluid collection assembly 100, according to an embodiment. The fluid collection assembly 100 includes a fluid impermeable barrier 102. The fluid impermeable barrier 102 includes a first end region 104 and a second end region 106 at an opposite end of the fluid collection assembly 100. The fluid impermeable barrier 102 also includes a sump 108 that forms at least a portion of the first end region 104. The sump 108 defines at least a portion of a fluid reservoir 110. The fluid collection assembly 100 also includes a sample port 112 extending from the sump 108. As such, the sample port 112 is in fluid communication with the fluid reservoir 110 and allows a sample to be taken of any of the bodily fluids that are present in the fluid reservoir 110.

The fluid impermeable barrier 102 defines at least one opening 114, such as a single elongated opening. The opening 114 is located between the first end region 104 and the second end region 106 of the fluid impermeable barrier 102. The opening 114 is configured to be positioned adjacent to a female urethral opening or a buried penis. The fluid impermeable barrier 102 also defines a chamber 116 that is in fluid communication with the opening 114 such that bodily fluids that are discharged by the urethral opening flow through the opening 114 and into the chamber 116. As previously discussed, the bodily fluids that are present in the chamber 116 generally flow towards the fluid reservoir 110. Additionally, the fluid impermeable barrier 102 defines a fluid outlet 118 that allows the bodily fluids to be removed from the fluid reservoir 110. In the illustrated embodiment, the fluid outlet 118 is located on the second end region 106 of the fluid impermeable barrier 102 while the fluid reservoir 110 is located at or near the first end region 104 of the fluid impermeable barrier 102. As such, the fluid collection assembly 100 may include at least one tube 120 positioned in the fluid outlet 118 that extends from the fluid outlet 118 to the fluid reservoir 110 thereby allowing the fluid outlet 118 to be in fluid communication with the fluid reservoir 110. The tube 120 may also extend from the fluid outlet 118 to another component of a fluid collection system, as will be discussed in more detail with regards to FIG. 6.

The fluid impermeable barrier 102 may be formed of any suitable material. For example, the fluid impermeable barrier 102 may be formed from silicone, another thermosetting polymer, another suitable fluid impermeable material, or combinations thereof. In an embodiment, as illustrated in FIGS. 1A and 1B, the fluid impermeable barrier 102 may be formed from a single piece. In an embodiment, the fluid impermeable barrier 102 may be formed from a plurality of pieces.

As previously discussed, the fluid impermeable barrier 102 includes a sump 108. The sump 108 may form the first end region 104 of the fluid impermeable barrier 102. The sump 108 includes portions of the fluid impermeable barrier 102 that at least one of defines the fluid reservoir 110 (shown in FIG. 1B), extends from the opening 114 to the first end region 104 of the fluid impermeable barrier 102, or is directly attached to the sample port 112. The sump 108 may be integrally formed with the rest of the fluid impermeable barrier 102 or may be formed separately from and attached to the rest of the fluid impermeable barrier 102.

At least a portion of the sump 108 may be at least partially transparent (e.g., translucent or transparent). For example, as previously discussed, the sump 108 defines the fluid reservoir 110 of the fluid collection assembly 100. Selecting at least a portion of the sump 108 to be at least partially transparent allows a user (e.g., medical practitioner) to determine when bodily fluids are present in the fluid reservoir 110. As such, the at least partially transparent portions of the sump 108 allows the user to determine when samples of the bodily fluids may be taken. In an embodiment, the at least partially transparent portion of the sump 108 may also include one or more markings (not shown) thereon. The markings formed on the sump 108 may indicate the volume of the bodily fluids that are present in the fluid reservoir 110. In an example, the markings quantitatively (e.g., in milliliters, fluid ounces, etc.) indicate the volume of the bodily fluids that are present in the fluid reservoir 110. In an example, the markings qualitatively indicate the bodily fluids that are present in the fluid reservoir. In such an embodiment, the markings may indicate when a sufficient quantity of fluids are present in the fluid reservoir 110 to obtain a sample. Examples of transparent material that may form at least a portion of the sump 108 include glass, one or more transparent polymers (e.g., polycarbonate, acrylic, polyethylene terephthalate, polyethylene, etc.), or combinations thereof. In an embodiment, at least a portion of the sump 108 may be at least partially opaque to minimize patient embarrassment.

As previously discussed, the sample port 112 is attached to the sump 108. For example, the sump 108 may define an hole 122 that is adjacent to the fluid reservoir 110. The sample port 112 is attached to the portions of the sump 108 about the hole 122. This allows the sample port 112 to be in fluid communication with the fluid reservoir 110 via the hole 122. Generally, the hole 122 is located at or near the first end region 104 of the fluid impermeable barrier 102 since the first end region 104 is generally at or near the gravimetric low point of the fluid collection assembly 100 during use of the fluid collection assembly 100. As such, even in the absence of a suction force, any bodily fluids that enter the chamber 116 are drawn towards the fluid reservoir 110 and the hole 122.

In an embodiment, as illustrated, the hole 122 is located near (but not at) the first end region 104. Instead, the hole 122 may be located on a back surface 123 of the fluid impermeable barrier 102. The back surface 123 of the fluid impermeable barrier 102 is a surface of the fluid impermeable barrier 102 that is opposite or generally opposite the opening 114 defined by the fluid impermeable barrier 102. Forming the hole 122 on the back surface 123 of the fluid impermeable barrier 102 may facilitate obtaining a sample more effectively than if the hole 122 was formed on another surface of the fluid impermeable barrier 102. For example, during operation, the opening 114 of the fluid impermeable barrier 102 is positioned adjacent to the urethral opening of the individual. As such, any front surface 121 of the fluid impermeable barrier 102 (i.e., any surface of the fluid impermeable barrier 102 that faces the same direction as the opening 114) is likewise positioned adjacent to the urethral opening, mons pubis, or perineal regions of the individual thereby making access to the front surface 121, for the purpose of obtaining a sample, difficult. Further, any side surface 125 of the fluid impermeable barrier 102 (i.e., any surface of the fluid impermeable barrier 202 between the front surface 121 and the back surface 123) is likely to be positioned adjacent or proximate to the thighs of the individual making access to these surface with a fluid collector difficult. Additionally, the first end region 104 of the fluid impermeable barrier 102 may be positioned adjacent to or proximate to a bed when the individual using the fluid collection assembly 100 is lying down thereby making it difficult to access the first end region 104 with a fluid collector. Meanwhile, the back surface 123 of the fluid impermeable barrier 102 may be easily accessible with a fluid collector, especially if the individual using the fluid collection assembly 100 opens their legs slightly. However, it is noted that the hole 122 may be located on any suitable surface of the sump 108, such as at the first end region 104, on the front surface 121 of the sump 108, or on a side surface 125 of the sump 108, without limitation.

The sample port 112 includes an attachment portion 124 that is configured to be attached to the portions of the sump 108 that are around the hole 122. The attachment portion 124 may be attached to the sump 108 using any suitable technique. In an embodiment, the attachment portion 124 is attached to the sump 108 using ultrasonic welding which forms molecular bonds or other strong attachment forces between the attachment portion 124 and the sump 108. However, in some embodiments, the attachment portion 124 may only be attached to the sump 108 using ultrasonic welding when both the attachment portion 124 and the sump 108 are thermoplastic and both the attachment portion 124 and the sump 108 are compatible, which is not always the case. In an embodiment, the attachment portion 124 is configured to be attached to the sump 108 via heat staking. In such an embodiment, the attachment portion 124 is attached to the fluid impermeable barrier 102 via heat staking. In such an embodiment, one of the attachment portion 124 or the portion of the sump 108 that is configured to be attached to the attachment portion 124 includes one or more protrusions while the other of the attachment portion 124 or the portion of the sump 108 that is configured to be attached to the attachment portion 124 defines passageways extending therethrough that are configured to receive respectively ones of the one or more protrusions. After positioning the protrusions through the passageways, pressure and heat are applied to the protrusions which deforms the protrusions into "stakes" that exhibit a general mushroom-like shape. The stakes are then cooled such that the stakes maintain the shape thereof. One benefit of attaching the attachment portion 124 to the sump 108 using heat staking is that the materials that form the attachment portion 124 and the sump 108 do not have to be compatible (unlike ultrasonic welding) and only one of the attachment portion 124 or the sump 108 have to be a thermoplastic material. As such, heat staking may be used to attach the attachment portion 124 to the sump 108 when the attachment portion 124 and the sump 108 include dissimilar materials, though heat staking may also be used when the attachment portion 124 and the sump 108 include similar materials. In an embodiment, the attachment portion 124 may be attached to the sump 108 using other suitable techniques, such as with an adhesive.

In an embodiment, the attachment portion 124 defines a port opening 126 that allows the bodily fluids to flow through the hole 122 and into/through the sample port 112. For example, the attachment portion 124 may exhibit a generally annular shape or other similar shape which may provide a surface to be attached to the sump 108 in a fluid tight manner while also defining the port opening 126.

The sample port 112 includes a valve 128. As used herein, the valve 128 includes any suitable mechanism that is configured to switch between a closed state that restricts fluid flow therethrough and an open state that permits fluid flow therethrough. In an embodiment, the valve 128 may be a split septum fitting that includes a deformable flexible material defining an gap 130 (e.g., slit, pin hole, etc.). The valve 128 may be configured such that the gap 130 is sufficiently small that fluid cannot flow therethrough (e.g., the gap 130 is defined by a hydrophobic material) when the valve 128 is in a relaxed state (i.e., closed state). However, pressing against the valve 128 with, for example, a fluid collector causes the flexible material of the valve 128 to deform and increase the size of the gap 130 such that fluid may flow through the gap 130. Removing the pressure applied to the valve 128 may cause the gap 130 to decrease in size such that the gap 130 again exhibits a size sufficiently small that fluid cannot flow therethrough. In an embodiment, the valve 128 includes a plastic layer (e.g., a plastic membrane) extending across an opening thereof (e.g., the port opening 126). The plastic layer may not initially define a gap. However, a syringe may easily penetrate the plastic layer to form a gap. However, the gap may exhibit a size, after removal of the syringe, that is sufficiently small that fluid cannot flow therethrough (e.g., the plastic layer is formed of a hydrophobic material). In an embodiment, the valve 128 may include a mechanical valve that switches between the open and closed states thereof responsive to actuation of an actuator. For example, the valve 128 may include a butterfly valve, a ball valve, or any other suitable mechanical valve.

In an embodiment, the valve 128 is spaced from the attachment portion 124. In such an embodiment, the sample port 112 may include at least one wall 132 extending from the attachment portion 124 to the valve 128. The wall 132 may define a passageway 134 extending from the port opening 126 to the valve 128. The wall 132 may facilitate attachment of a fluid collector to the sample port 112. In an example, the wall 132 may include one or more threads 136 formed therein. The threads 136 may secure the fluid collector to the sample port 112 while taking a sample. The threads 136 may also allow the connection device to be connected to the sample port 112 by twisting (e.g., without applying a pressure to the sump 108) which may prevent contraction of the sump 108. In an example, the wall 132 allows the fluid collector to be attached to the sample port 112 using a luer lock mechanism.

The fluid collection assembly 100 includes at least one wicking material 138 disposed in the chamber 116. In the illustrated embodiment, referring to FIG. 1B, the wicking material 138 includes a fluid permeable support 140 and a fluid permeable membrane 142. The fluid reservoir 110, the fluid permeable support 140, and the fluid permeable membrane 142 may be arranged such that any bodily fluids flowing through the opening 114 flows through the fluid permeable membrane 142, through the fluid permeable support 140, and into the fluid reservoir 110. The bodily fluids may then flow from the fluid reservoir 110 to the tube 120 thereby removing the bodily fluids from the chamber 116.

The fluid permeable support 140 can be positioned relative to the permeable membrane 142 such that the fluid permeable support 140 maintains the permeable membrane 142 in a particular shape. In an embodiment, the fluid permeable support 140 can be configured to maintain the permeable membrane 142 against or near the urethral opening of the individual. For example, the fluid permeable support 140 can include a portion having a curved shape in contact with the permeable membrane 142 such that the permeable membrane 142 is also curved, thus creating a comfortable and secure interface for engagement with the urethral opening and/or the area of the body near the urethral opening.

In an embodiment, the fluid permeable support 140 can be made of a rigid plastic. In an embodiment, the fluid permeable support 140 can have any suitable shape and be formed of any suitable material. For example, the fluid permeable support 140 can be flexible. Additionally, the fluid permeable support 140 can be formed of aluminum, a composite of plastic and aluminum, some other metal and/or a composite. In an embodiment, the fluid permeable support 140 can be formed of a natural material, such as, for example, plant fibers (e.g., Greener Clean manufactured by 3M®). The natural material can include openings that allow fluid to flow through the natural material. In an embodiment, the fluid permeable support 140 can be cylindrical and can define a lumen. In an embodiment, the fluid permeable support 140 can be formed of perforated coated paper, such as tubular waxed paper. In an embodiment, the fluid permeable support 140 may be formed from spun plastic, such as non-woven permeable nylon and/or polyester webbing.

The fluid permeable membrane 142 can be formed of a material that is permeable to the bodily fluids and has wicking properties. The fluid permeable membrane 142 can have a high absorptive rate and a high permeation rate such that the bodily fluids can be rapidly absorbed by the fluid permeable membrane 142 and/or transported through the fluid permeable membrane 142. In an embodiment, the fluid permeable membrane 142 can be a ribbed knit fabric. In an embodiment, the fluid permeable membrane 142 can include and/or have the moisture-wicking characteristic of gauze, felt, terrycloth, thick tissue paper, and/or a paper towel. In an embodiment, the fluid permeable membrane 142 can be soft and/or minimally abrasive such that the fluid permeable membrane 142 does not irritate the skin of the user. The fluid permeable membrane 142 can be configured to wick bodily fluids away from the urethral opening and/or the skin of the individual such that the dampness of the skin of the individual is lessened and infections are prevented. Additionally, the wicking properties of the fluid permeable membrane 142 can help prevent bodily fluids from leaking or flowing beyond the assembly onto, for example, a bed. In an embodiment, the fluid permeable membrane 142 can be formed of fine denier polyester fibers coated with a thermoplastic water-based binder system.

In an embodiment, the at least one of the fluid permeable support 140 or the fluid permeable membrane 142 may be omitted from the fluid collection assembly 100 such that the wicking material 138 only includes a single material. In an embodiment, the wicking material 138 may include three or more materials, such as the fluid permeable support 140, the fluid permeable membrane 142, and at least one additional material. Regardless, one or more components of the wicking material 138 may include permeable material designed to wick or pass fluid therethrough. The permeable properties referred to herein may be wicking, capillary action, diffusion, or other similar properties or processes, and are referred to herein as "permeable" and/or "wicking." Such "wicking" may not include absorption of one or more components of the bodily fluids (e.g., urine) into the one or more components of the wicking material 138. Put another way, substantially no absorption of one or more components of the bodily fluids into the one or more components of the wicking material 138 may take place after the wicking material 138 is exposed to the bodily fluids. While no absorption is desired, the term "substantially no absorption" may allow for nominal amounts of absorption of one or more components of the bodily fluids into the wicking material 138 (e.g., absorbency), such as less than about 10 wt % of the dry weight of the wicking material 138, less than about 7 wt %, less than about 5 wt %, less than about 3 wt %, less than about 2 wt %, less than about 1 wt %, or less than about 0.5 wt % of the dry weight of the wicking material 138. In an embodiment, the fluid collection assembly 100 may include one or more absorbent or adsorbent materials instead of or in addition to the wicking material 138.

Additional examples of fluid collection assemblies are disclosed in U.S. Pat. No. 10,226,376 filed on Jun. 1, 2017, the disclosure of which is incorporated herein, in its entirety, by this reference.

As will be discussed in more detail with regards to FIG. 6, the fluid collection assembly 100 may be in fluid communication with a fluid storage container and a vacuum source. For example, the fluid outlet 118 may be coupled to at least one tube 120 and the tube 120 may fluidly couple the fluid collection assembly 100 to the fluid storage container and the vacuum source. The tube 120 may also extend behind the wicking material 138 such that the tube 120 is positioned in or near the fluid reservoir 110.

Figure 1C:
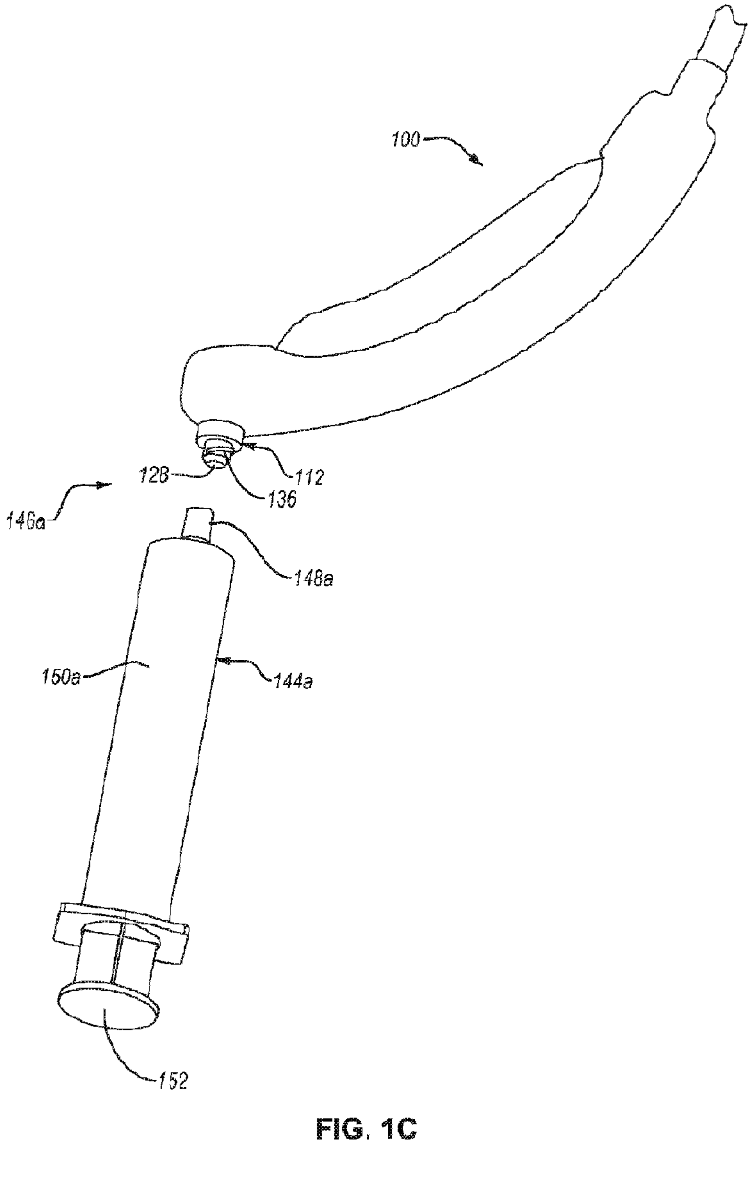
FIGS. 1C and 1D are isometric views of a portion of different fluid collection systems, according to different embodiments.
Figure 1D:
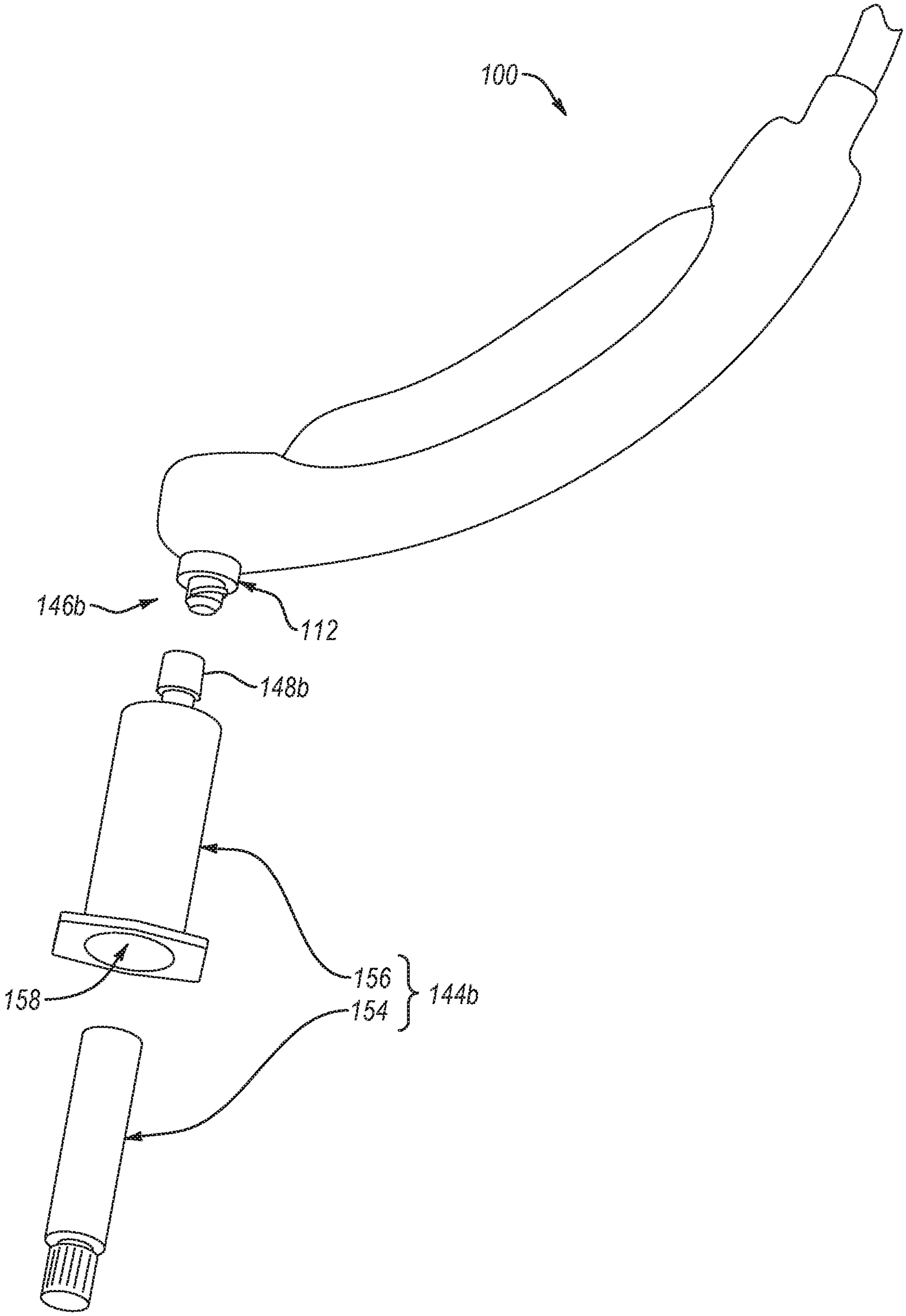

The fluid collection assembly 100 may form part of a fluid collection system that includes at least one fluid collector. For example, FIGS. 1C and 1D are isometric views of a portion of different fluid collection systems, according to different embodiments. The fluid collection systems illustrated in FIGS. 1C and 1D include the fluid collection assembly 100 and different fluid collectors. Although FIGS. 1C and 1D illustrate fluid collection systems including the fluid collection assembly 100 illustrated in FIGS. 1A and 1B, it is noted that the illustrated fluid collection systems may include any of the fluid collection assemblies disclosed herein.

Referring to FIG. 1C, the fluid collector 144*a* of the fluid collection system 146*a* includes a needleless syringe that is configured to connect to the sample port 112. For example, the fluid collector 114*a* includes a collector port 148*a* that is configured to connect with the sample port 112. For example, the collector port 148*a* may connect with the sample port 112 in a fluid tight manner. The collector port 148*a* may also be configured to be secured to the sample port 112 to prevent inadvertently disconnecting the collector port 148*a* from the sample port 112. For example, the collector port 148*a* may include one or more threads (not shown, obscured) that are configured to mate with the threads 136 of the sample port 112. In an embodiment, the sample port 112 and the collector port 148*a* may form a luer-lock connection. In an embodiment, the collector port 148*a* may be configured to switch the valve 128 of the sample port 112 from the closed state thereof to the open state thereof when the collector port 148*a* is connected to the sample port 112.

The fluid collector 144*a* may also include a fluid reservoir 150*a* that is in fluid communication with the collector port 148*a*. For example, the fluid reservoir 150*a* may receive any bodily fluids that are received by the collector port 148*a*. The fluid collector 144*a* may also include a plunger 152 connected to the fluid reservoir 150*a*. The plunger 152 may be configured to selectively pull bodily fluids through the collector port 148*a* and into the fluid reservoir 150*a* and/or push the bodily fluids from the fluid reservoir 150*a* and through the collector port 148*a* responsive to manipulation of the plunger 152 by an user of the fluid collector 144*a*.

Referring to FIG. 1D, the fluid collector 144*b* of the fluid collection system 146*b* includes a vial 154. The vial 154 may be initially under vacuum such that connecting the vial 154 to the sample port 112 pulls any bodily fluids from the fluid reservoir 110 of the fluid collection assembly 100 into the vial 154. In an embodiment, not shown, the vial 154 is configured to be directly connected to the sample port 112, In an embodiment, as illustrated, the vial 154 is configured to be indirectly connected to the sample port 112 using an intermediary device 156. The intermediary device 156 may include a collector port 148*b* that is the same or similar to the collector port 148*b*. The intermediary device 156 may also define a receptacle 158 that is configured to receive at least a portion of the vial 154.

It is noted that the fluid collection systems disclosed herein may be used with fluid collectors other than the fluid collectors illustrated in FIGS. 1C, and 1D. For example, the fluid collection systems disclosed herein may include a needle syringe or any other suitable fluid collector.

Referring to FIGS. 1A to 1D, during use, the fluid collection assembly 100 is positioned such that the opening 114 is adjacent to the urethral opening of an individual. The fluid collection assembly 100 may then receive bodily fluids from the urethral opening of the individual through the opening, into the chamber 116 (e.g., into the at least one wicking material 138), and to the fluid reservoir 110. The bodily fluids may then be removed from the fluid reservoir 110 through the tube 120 using a suction force. Samples of the bodily fluids may be obtain by connecting a fluid collector (e.g., fluid collector 144*a* or fluid collector 144*b*) and extracting the bodily fluids from the fluid reservoir 110 into the fluid collector. In an embodiment, the sample of the bodily fluids may be extracted from the fluid reservoir 110 while a suction force is applied from the tube 120 to the fluid reservoir 110. However, the suction force that is applied from the tube 120 to the fluid reservoir 110 may limit the quantity of bodily fluids that are obtained. As such, in an embodiment, the suction force is turned off at least while the sample is extracted from the fluid reservoir 110. The suction force may be turned off by kinking the tube 120, turning off the vacuum source, etc. Turning off the suction force may allow the bodily fluids to pool in the fluid reservoir and may prevent the removal of the bodily fluids until after the sample is obtained.

Figure 2:
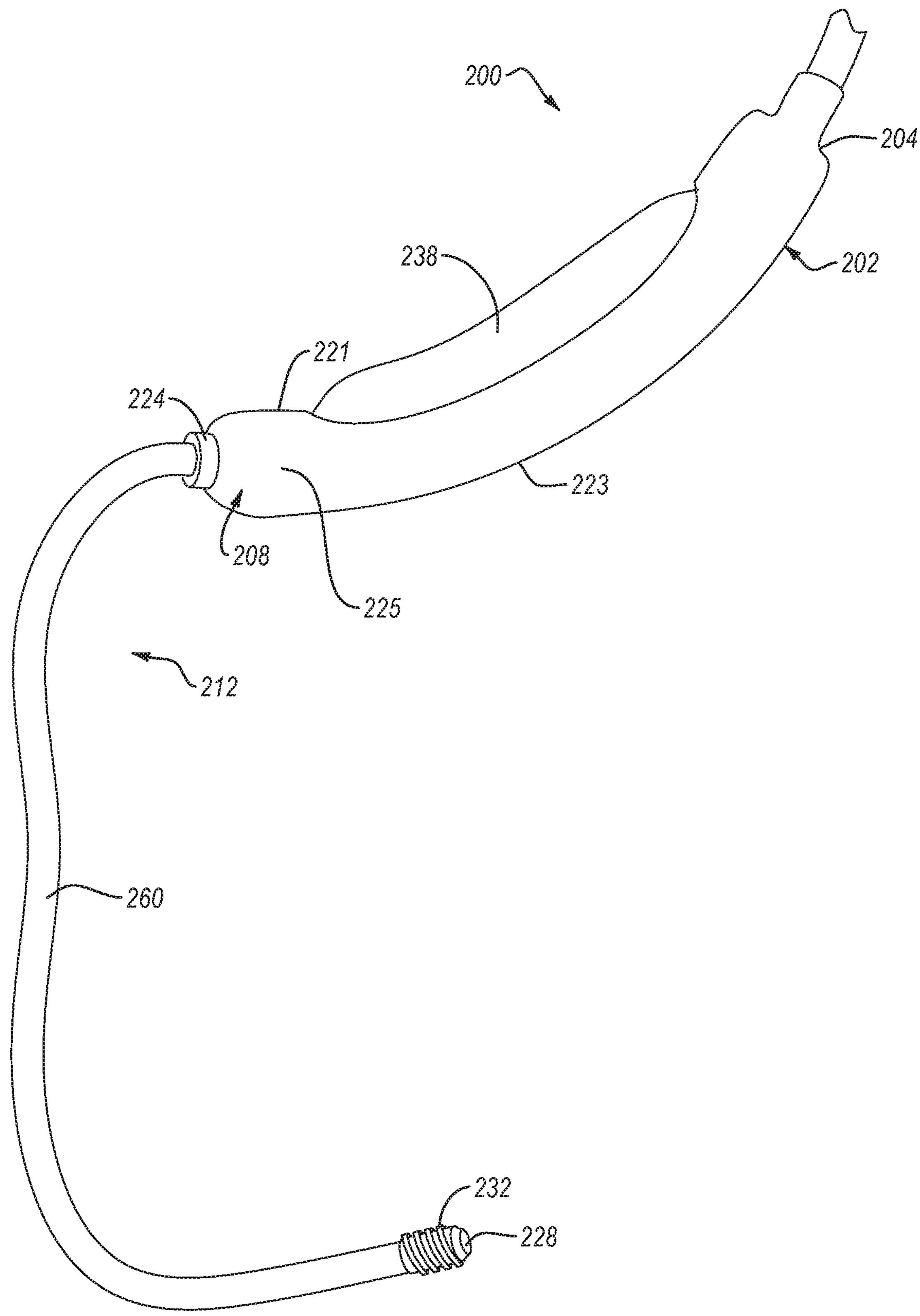
FIG. 2 is an isometric view of a fluid collection assembly, according to an embodiment.

FIG. 2 is an isometric view of a fluid collection assembly 200, according to an embodiment. Except as otherwise disclosed herein, the fluid collection assembly 200 is the same or substantially similar to any of the fluid collection assemblies disclosed herein. For example, the fluid collection assembly 200 may include a fluid impermeable barrier 202 extending between the first end region 204 and a second end region 206, at least one wicking material 238 disposed in a chamber defined by the fluid impermeable barrier 202, and a sample port 212.

The sample port 212 includes an attachment portion 224. As previously discussed, the attachment portion 224 may be attached to any portion of the sump 208. In the illustrated embodiment, the attachment portion 224 is attached to the first end region 204 of the fluid impermeable barrier 202, though it is noted that the attachment portion 224 may be attached to another portion of the sump 208 (e.g., front surface 221, a back surface 223, or a side surface 225). The sample port 212 also include a valve 228 and, optionally, at least one rigid wall 232.

As previously discussed, certain regions of the sump 208 may be difficult to access with a fluid collector when the fluid collection assembly 200 is positioned adjacent to the urethral opening of the individual. For example, the first end region 204 may be difficult to access when the individual is lying down or sitting because the front surface 221 of the fluid impermeable barrier 202 is adjacent or proximate to the urethral opening, the side surface 225 of the fluid impermeable barrier 202 may be adjacent to the thighs of the individual, and the back surface 223 may be difficult to access if the individual's legs are closed. It is noted that the legs of the individual may need to remain closed (thereby preventing access to the back surface 223) to keep the fluid collection assembly 200 adjacent to the urethral opening and to prevent leaks of the bodily fluids. To resolve these issues, in the illustrated embodiment, the sample port 212 includes a tube 260 extending from the attachment portion 224 to the valve 228 (e.g., to the wall 232). The tube 260 defines a passageway (not shown, obscured) that allows the attachment portion 224 to be in fluid communication with the valve 228 such that the valve 228 may remove bodily fluids from the fluid reservoir (not shown, obscured). Generally, the tube 260 is flexible thereby allowing the valve 228 to be moved to a location that is easily accessible.

The tube 260 may exhibit any suitable length. For example, the tube 260 may exhibit a length that is greater than about 2.5 cm, greater than about 5 cm, greater than about 7.5 cm, greater than about 10 cm, greater than about 12.5 cm, greater than about 15 cm, greater than about 20 cm, greater than about 25 cm, greater than about 30 cm, greater than about 40 cm, greater than about 50 cm, greater than about 60 cm, greater than about 70 cm, greater than about 80 cm, greater than about 90 cm, greater than about 1 m, greater than about 1.5 m, greater than about 2 m, or in ranges of about 2.5 cm to about 7.5 cm, about 5 cm to about 10 cm, about 7.5 cm to about 12.5 cm, about 10 cm to about 15 cm, about 12.5 cm to about 20 cm, about 15 cm to about 25 cm, about 20 cm to about 30 cm, about 25 cm to about 40 cm, about 30 cm to about 50 cm, about 40 cm to about 60, about 50 cm to about 70 cm, about 60 cm to about 80 cm, about 70 cm to about 90 cm, about 80 cm to about 1 m, about 90 cm to about 1.5 m, or about 1 m to about 2 m. The length of the tube 260 may be selected based on a number of factors. In an example, the length of the tube 260 may be selected on the size of the individual wherein larger individuals (e.g., more obese, tall, or otherwise larger individuals) may require the tube 260 to exhibit a longer length than when the individual is smaller. In an example, the length of the tube 260 may be selected based on which region of the sump 208 the sample port 212 is attached. In an example, the tube 260 may need to exhibit a longer length when the sample port 212 is attached to the first end region 204 than when the sample port 212 is attached to the back surface 223 since the first end region 204 may be spaced further from an easily accessible location than the back surface 223. In an example, the length of the tube 260 may be selected based on the size of the fluid reservoir since increasing the length of the tube 260 increases the amount of bodily fluids the tube 260 may store therein. As such, the tube 260 may exhibit an increased length when used with a small fluid reservoir than when the tube 260 is used with a large fluid reservoir.

The fluid reservoir of the fluid collection assemblies disclosed herein are configured to hold bodily fluids therein until the bodily fluids are removed using a suction force from a tube. Generally, the suction three from the tube removes the bodily fluids quickly from the fluid reservoir. However, kinking the tube or otherwise stopping the suction force may cause the bodily fluids to pool in the fluid reservoir. Thus, in some embodiments, the fluid reservoir disclosed herein may need to exhibit a volume that is greater than similar conventional fluid collection assemblies to prevent overfilling the fluid reservoir since overfilling the fluid reservoir may cause the bodily fluids to leak from the chamber. For example, the fluid reservoirs of the fluid collection assemblies disclosed herein may exhibit a volume that is greater than 15 milliliters ("mL"), greater than about 30 mL, greater than about 50 mL, greater than about 75 mL, greater than about 100 mL, greater than about 150 mL, greater than about 200 mL, greater than about 250 mL, greater than about 300 mL, greater than about 400 mL, greater than about 500 mL, greater than about 600 mL, greater than about 700 mL, greater than about 800 mL, or in ranges of about 15 mL to about 50 mL, about 30 mL to about 75 mL, about 50 mL to about 100 mL, about 75 mL to about 150 mL, about 100 mL to about 200 mL, about 150 mL to about 250 mL, about 200 mL to about 300 mL, about 250 mL to about 400 mL, about 300 mL to about 500 mL, about 400 mL to about 600 mL, about 500 mL to about 700 mL, or about 600 mL to about 800 mL.

The volume of the fluid reservoir may depend on a number of factors. In an example, the volume of the fluid reservoir may depend on whether the individual using the fluid collection assembly can control urination. For instance, an individual who has no control over urination may urinate more often than an individual who has control over urination. As such, the volume of a fluid reservoir may be smaller (e.g., less than 400 mL, less than 300 mL, or less than 200 mL) for an individual who has no control over urination than the volume of a fluid reservoir for an individual who has control over urination. It is noted that an individual who has control over urination may still use a fluid collection assembly with a volumetrically small fluid reservoir when the individual is given direction to urinate frequently. In an example, the volume of the fluid reservoir may depend on whether the suction force is expected to be stopped to obtain a sample since not stopping the suction force allows the fluid reservoir to exhibit a relatively small volume. In an example, the volume of the fluid reservoir may be selected based on the expected size of the bladder of the individual. For instance, a child or a smaller individual may use a fluid collection assembly having a relatively small fluid reservoir compared to larger individuals. In an example, as previously discussed, the size of the fluid reservoir may depend on whether the sample port includes a tube and the relative length of the tube.

Figure 3A:
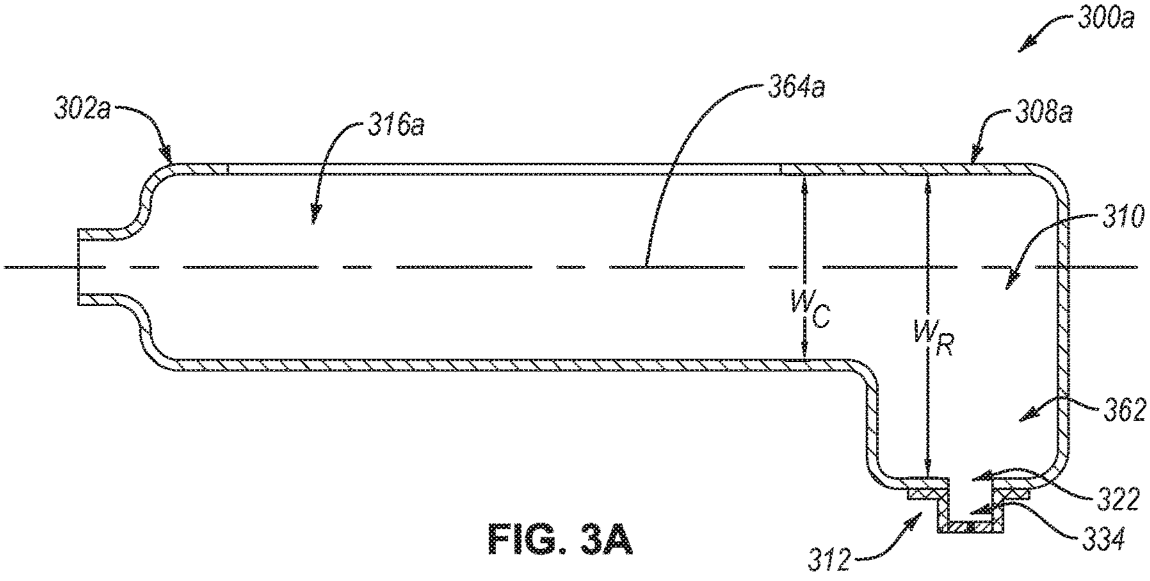
FIG. 3A is a schematic cross-sectional view of a fluid collection assembly, according to an embodiment.

The fluid collection assemblies may exhibit a variety of different structures that allow the fluid reservoirs to exhibit the volumes disclosed herein. For example, FIG. 3A is a schematic cross-sectional view of a fluid collection assembly 300*a*, according to an embodiment. Except as otherwise disclosed herein, the fluid collection assembly 300*a* is the same or substantially similar to any of the fluid collection assemblies disclosed herein. For example, the fluid collection assembly 300*a* includes a fluid impermeable barrier 302*a* defining a chamber 316*a*. For clarity, the chamber 316*a* is illustrated as being empty. However, it is noted that one or more elements may be disposed in the chamber 316*a*, such as at least one wicking material.

The fluid impermeable barrier 302*a* includes a sump 308*a* defining a fluid reservoir 310*a*. The sump 308*a* defines a bulge 362 which increases the volume of the fluid reservoir 310*a*. For example, the bulge 362 may cause the fluid reservoir 310*a* defined to exhibit a maximum reservoir width $W_R$ that is measured perpendicular to the longitudinal axis 364*a* of the fluid impermeable barrier 302*a*. It is noted that the maximum reservoir width $W_R$ does not extend into the hole 322 defined by the fluid impermeable barrier 302*a* or a passageway 334 defined by the sample port 312. The maximum reservoir width $W_R$ is greater than a maximum chamber width $W_C$ of the chamber 316*a*, wherein the maximum chamber width $W_C$ is measured at a location that is spaced from the fluid reservoir 310*a*. The greater width of the maximum reservoir width $W_R$ relative to the maximum chamber width $W_C$ increases the volume of the fluid reservoir 310*a* than if the fluid impermeable barrier 302*a* did not include the bulge 362.

In an embodiment, the maximum reservoir width $W_R$ may be greater than the maximum chamber width $W_C$ by at least a factor of about 1.25, at least a factor of about 1.5, at least a factor of about 1.75, at least a factor of about 2, at least a factor of about 2.5, at least a factor of about 3, at least a factor of about 3.5, at least a factor of about 4, or at least a factor of about 5. In an embodiment, the maximum reservoir width $W_R$ may be about 3 cm to about 4 cm, about 3.5 cm to about 4.5 cm, about 4 cm to about 5, about 4.5 cm to about 6 cm, about 5 cm to about 7 cm, about 6 cm to about 8 cm, about 7 cm to about 9 cm, about 8 cm to about 10, about 9 cm to about 11 cm, or greater than 10 cm and the maximum chamber width $W_C$ may be about 1 cm to about 3 cm, about 2 cm to about 4 cm, or about 3 cm to about 5 cm. The maximum reservoir width $W_R$ and the ratio of the maximum reservoir width $W_R$ to the maximum chamber width $W_C$ may be selected based on the desired volume of the fluid reservoir 310*a*.

Figure 3B:
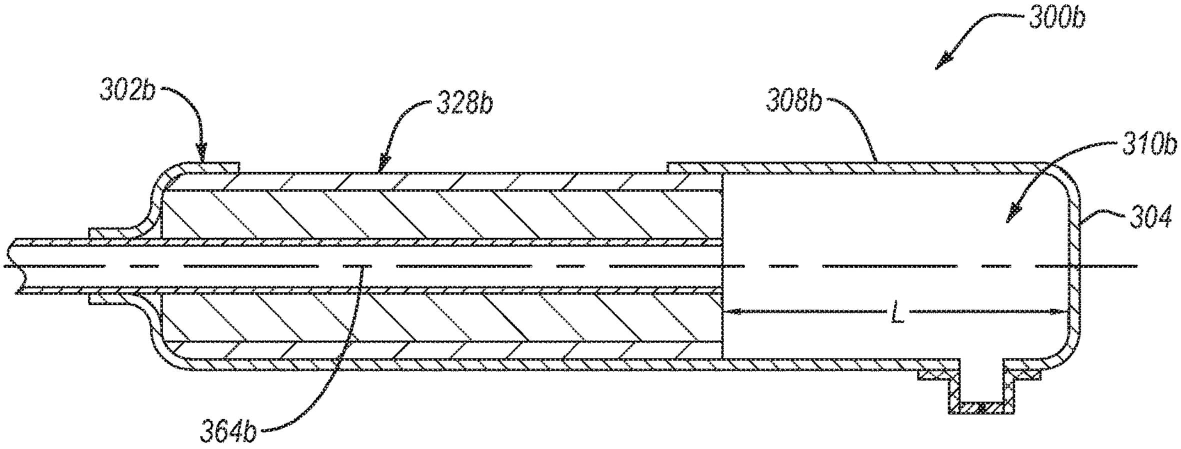
FIG. 3B is a schematic cross-sectional view of a fluid collection assembly having an elongated fluid reservoir, according to an embodiment.

Instead of increasing the width of the fluid reservoir, in an embodiment, the fluid reservoir may exhibit an elongated length. For example, FIG. 3B is a schematic cross-sectional view of a fluid collection assembly 300*b* having an elongated fluid reservoir 310*b*, according to an embodiment. Except as otherwise disclosed herein, the fluid collection assembly 300*b* is the same or substantially to any of the fluid collection assemblies disclosed herein. For example, the fluid collection assembly 300*b* may include a fluid impermeable barrier 302*b* and at least one wicking material 338*b*. The fluid impermeable barrier 302*b* may include a sump 308*b* defining the fluid reservoir 310*b*.

The fluid reservoir 310*b* (e.g., a substantially unoccupied fluid reservoir 310*b*) may exhibit a maximum length L. The maximum length L may be measured from the at least one wicking material 338*b* to the first end region 304 of the fluid impermeable barrier 302*b*. For example, the maximum L of the fluid reservoir 310*b* may be measured parallel to a longitudinal axis 364*b* of the of the fluid impermeable barrier 302*b*. Increasing the maximum length L of the fluid reservoir 310*b* increases the volume of the fluid reservoir 310*b* thereby increasing the quantity of bodily fluids that may be stored in the fluid reservoir 310*b*.

The maximum length L of the fluid reservoir 310*b* may be greater than the length of fluid reservoirs of conventional fluid collection assemblies. In an embodiment, the maximum length L may be greater than about 3 cm, greater than about 4 cm, greater than about 5 cm, greater than about 6 cm, greater than about 7 cm, greater than about 8 cm, greater than about 9 cm, greater than about 10 cm, greater than about 12.5 cm, greater than about 15 cm, or in ranges of about 3 cm to about 5 cm, about 4 cm to about 6 cm, about 5 cm to about 7 cm, about 6 cm to about 8 cm, about 7 cm to about 9 cm, about 8 cm to about 10 cm, about 9 cm to about 12.5 cm, or about 10 cm to about 15 cm. The maximum length L of the fluid reservoir 310*b* may be selected based on the desired volume of the fluid reservoir 310*b*.

As previously discussed, the fluid impermeable barriers disclosed herein may be at least partially formed from silicone or another easily deformable material. Such fluid impermeable barriers allow the fluid collection assemblies disclosed herein to be fitted to an individual. For example, the curvature and topography of the region about the urethral opening may be different for different individuals. The easily deformable fluid impermeable barrier allows the fluid collection assembly to easy conform to the curvature and topography of each individual. However, the easily deformable material of the fluid impermeable barrier may inadvertently deform when a fluid collector is connected to the sample port. When bodily fluids are present in the fluid reservoir, inadvertently deforming the fluid impermeable barrier may decrease the volume of the fluid reservoir and cause the bodily fluids to leak from the chamber.

In an embodiment, the leakage caused by connecting the fluid collector to the sample port may be mitigated by connecting the fluid collector to the sample port before bodily fluids are present in the fluid reservoir (e.g., before stopping the suction force). In an embodiment, the inadvertent deformation may be mitigated by using threads to connect the fluid collector to the sample port since the force required to tread the fluid collector onto the sample port, if performed properly, may only deform the fluid impermeable barrier an insignificant amount. In an embodiment, the attachment portion of the sample port may exhibit a large diameter (e.g., may extend radially outwardly from the walls of the sample port) that mitigates any deformation by spreading any force caused by connecting the fluid collector to the sample port over a larger area of the fluid impermeable barrier.

Figure 4A:
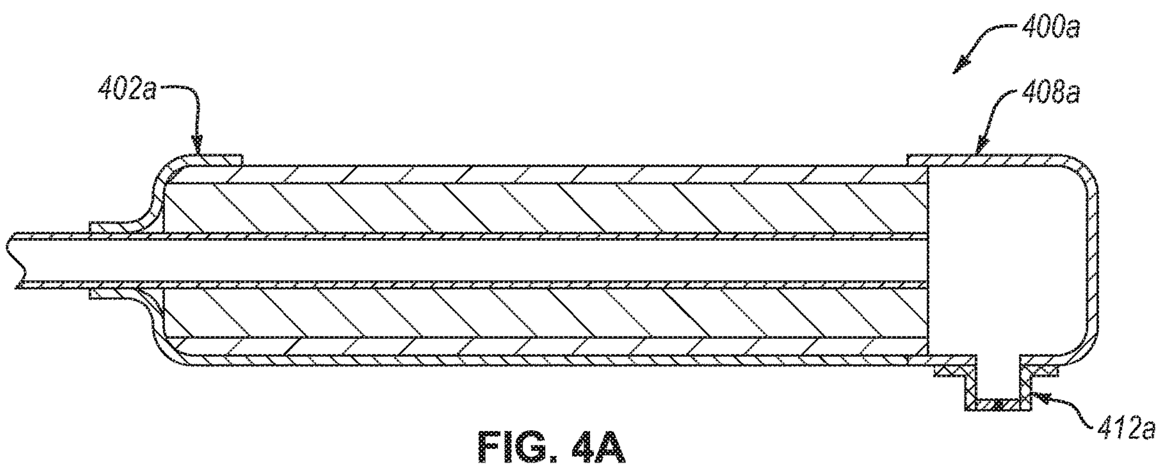
FIGS. 4A to 4C are schematic cross-sectional views of fluid collection assemblies including sumps exhibiting a greater rigidity than the rest of the fluid impermeable barriers thereof, according to different embodiments.
Figure 4B:
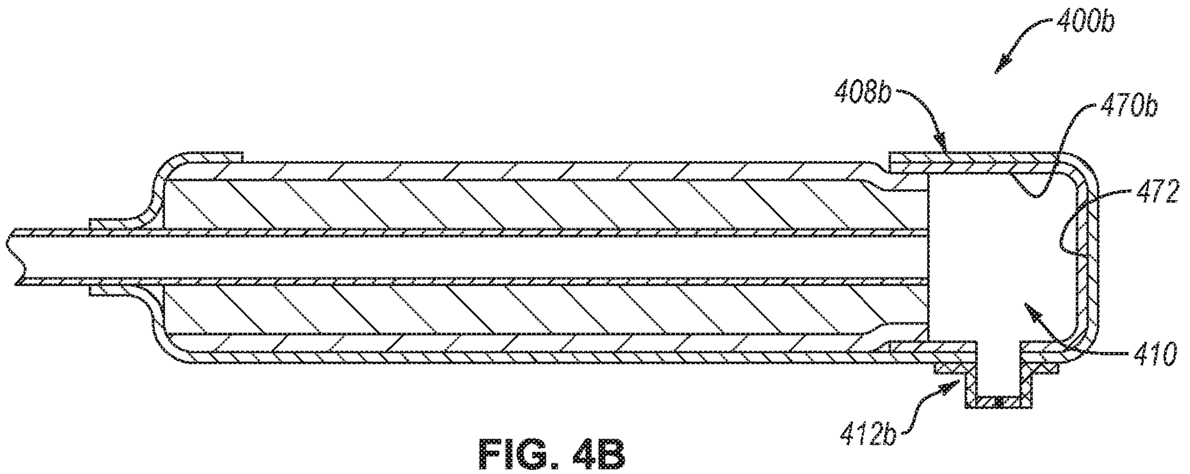
Figure 4C:
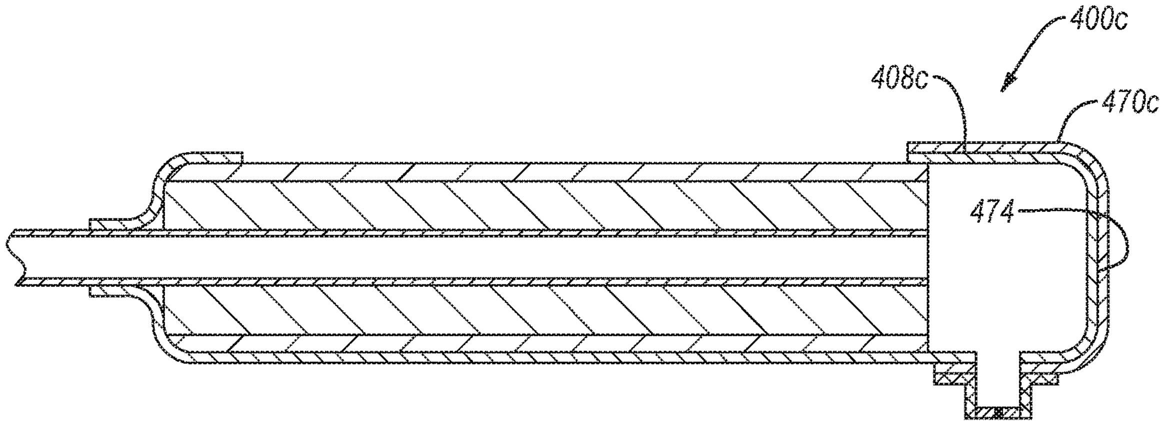

In an embodiment, the inadvertent deformation of the fluid impermeable barrier may be mitigated by increasing the rigidity of the sump relative to the rest of the fluid impermeable barrier. For example, FIGS. 4A to 4C are schematic cross-sectional views of fluid collection assemblies including sumps exhibiting a greater rigidity (i.e., better to resist deformations) than the rest of the fluid impermeable barriers thereof, according to different embodiments. Except as otherwise disclosed herein, the fluid collection assemblies illustrated in FIGS. 4A-4C are the same or substantially similar to any of the fluid collection assemblies disclosed herein.

Referring to FIG. 4A, the sump 408*a* itself (i.e., without any support structure) exhibits a rigidity that is greater than the rest of the fluid impermeable barrier 402*a* of the fluid collection assembly 400*a*. For example, the sump 408*a* may be distinct from the rest of the fluid impermeable barrier 402*a*. In an embodiment, as illustrated, the sump 408*a* may be formed from a material that is different than and exhibits an elasticity (i.e., Young's modulus) that is greater than the rest of the fluid impermeable barrier 402*a*. The increased elasticity of the sump 408*a* may allow the sump 408*a* to better resist deformation when the fluid collector is attached to the sample port 412*a*. Examples of material that may form the scrip 408*a* and may exhibit an elasticity greater than the rest of the fluid impermeable barrier 402*a* includes epoxy, polyacetal, polyester, metal, or any other suitable material. Since the sump 408*a* is formed from a different material than the rest of fluid impermeable barrier 402*a*, the sump 408*a* may be attached to the rest of the fluid impermeable barrier 402*a* using any suitable technique, such as with an adhesive, ultrasonic welding, heat staking, etc. In an embodiment, the sump 408*a* may exhibit a thickness that is greater than the rest of the fluid impermeable barrier 402*a*. The increased thickness of the sump 408*a* may increase the rigidity of the sump 408*a* and may allow the sump 408*a* to better resist deformation.

Referring to FIG. 4B, the fluid collection assembly 400*b* may include a support structure 470*b* that is configured to increase the rigidity of the sump 408*b*. The support structure 470*b* may exhibit a size that allows the support structure 470*b* to be disposed adjacent to an interior surface 472 of the sump 408*b*. In other words, the support structure 470*b* may be configured to be disposed in at least the fluid reservoir 410 and/or at least a portion of the support structure 470*b* exhibits a shape the corresponds to the shape of the interior surface 472 of the sump 408*b*. In an embodiment, the support structure 470*b* may be adjacent to an entirety of the interior surface 472 of the sump 408*b* or adjacent to only a portion of the interior surface 472 of the sump 408*b* (e.g., adjacent to the portion of the interior surface 472 that is proximate to the sample port 412*b*). In an embodiment, the support structure 470*b* may be adjacent to portions of the fluid impermeable barrier 402*b* that do not form part of the sump 408*b* in addition to being adjacent to at least a portion of the interior surface 472 of the sump 408*b*.

The support structure 470*b* is configured to support the sump 408*b* thereby increasing the rigidity of the sump 408*b*. In an embodiment, the support structure 470*b* is formed from a material exhibiting an elasticity (i.e., Young's modulus) that is greater than the sump 408*b*. For example, the support structure 470*b* may include epoxy, polyacetal, polyester, metal, or any other suitable material. In an embodiment, the support structure 470*b* is formed from a material exhibiting an elasticity that is equal to or less than the sump 408*b* since even such support structures increase the rigidity of the sump 408. In an embodiment, the support structure 470*b* is a solid plate (e.g., bent or molded plate). In an embodiment, the support structure 470*b* is a mesh since the mesh may be lighter than the solid plate which make the fluid collection assembly 400*b* easier to use without significantly decreasing the rigidity of the support structure 470*b*.

Disposing the support structure 470*b* in the fluid reservoir 410*b* may prevent the support structure 470*b* from coining in contact with an individual using the fluid collection assembly 400*b* which may make the fluid collection assembly 400*b* more comfortable to use. However, the presence of the support structure 470*b* in the fluid reservoir 410*b* may at least one of decrease the volume of the fluid reservoir 410*b*, compress the at least one wicking material 438, or require the at least one wicking material 438 to exhibit a non-cylindrical shape. As such, referring to FIG. 4C, is may be beneficial to form a fluid collection assembly 400*c* that includes a support structure 470*c* on at least a portion of an exterior surface 474 of the sump 408*c*. The support structure 470*c* may be the same as the support structure 470*b* of FIG. 4C except that the support structure 470*c* exhibits a shape that corresponds to at least a portion of the exterior surface 474. Further, the support structure 470*c* may include a coating (e.g., a silicone coating) that makes the support structure 470*c* more comfortable against the individual during use.

Figure 5:
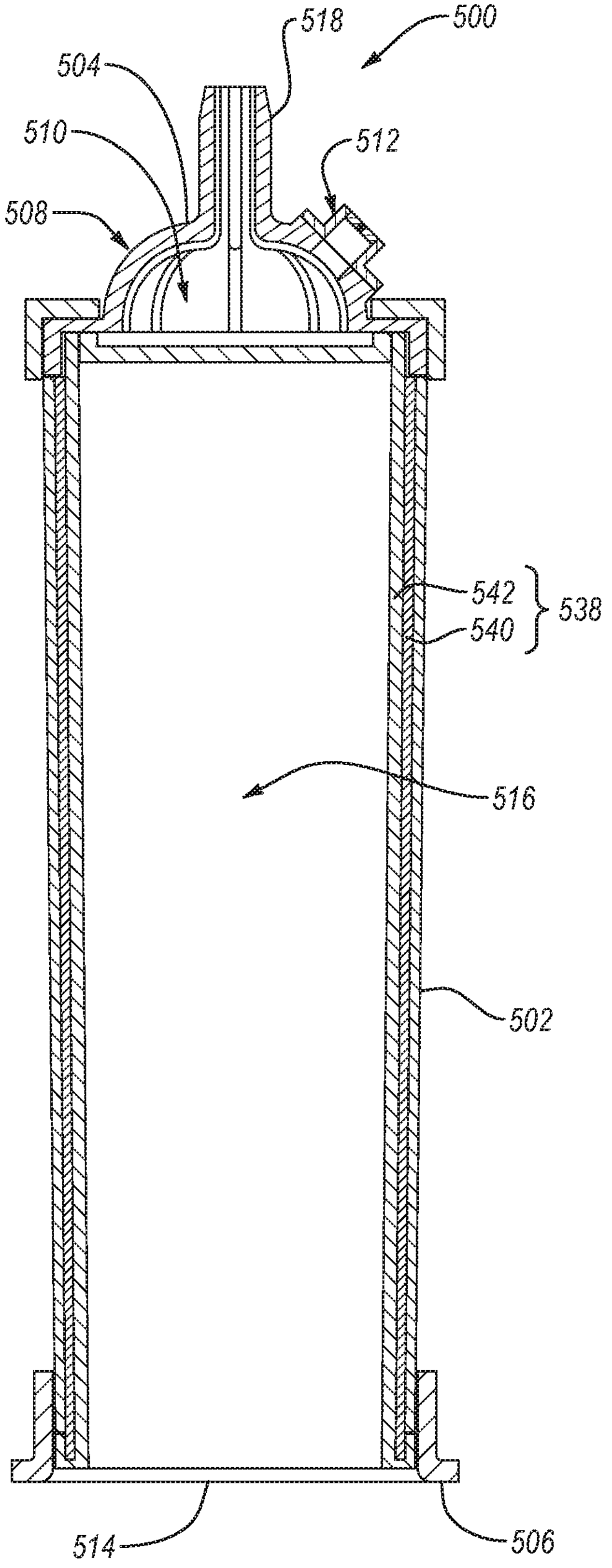
FIG. 5 is a schematic cross-sectional view of a fluid collection assembly defining an opening that is configured to receive a urethral opening, according to an embodiment.

The embodiments disclosed above are for fluid collection assemblies that are configured to receive bodily fluids from a female urethral opening or a buried penis. However, the principles and concepts disclosed herein may be used with fluid collection assemblies that are configured to have the openings thereof receive a urethral opening (e.g., male urethral opening) such that the urethral opening is disposed in the chamber. For example, FIG. 5 is a schematic cross-sectional view of a fluid collection assembly 500 defining an opening 514 that is configured to receive a urethral opening, according to an embodiment. Except as otherwise disclosed herein, the fluid collection assembly 500 may be the same or substantially similar to any of the fluid collection assemblies disclosed herein. For example, the fluid collection assembly 500 may include a fluid impermeable barrier 502 defining a chamber 516 and including a first end region 504, a second end region 506, and a sump 508 that forms the first end region 504. The fluid collection assembly 500 also includes a fluid outlet 518, a fluid reservoir 510, and the opening 514 at the second end region 506. The fluid collection assembly 500 may also include at least one wicking material 538 (e.g., a fluid permeable support 540 and a fluid permeable membrane 542) disposed in the chamber 516. The fluid collection assembly 500 may also include a sample port 512.

As previously discussed, the opening 514 is configured to receive the urethral opening. As such, the wicking material 538 does not extend across the opening 514. Instead, the wicking material 538 may exhibit a shape that corresponds to the shape of the fluid impermeable barrier 502 such that a portion of the chamber 516 is substantially unoccupied and the substantially unoccupied portion of the chamber 516 may receive the urethral opening. Further, the sample port 512 is attached to the sump 508. As such, the sample port 512 may be the same or substantially similar to any of the sample ports disclosed herein.

Additional examples of fluid collection assemblies that include an opening that is configured to receive a urethral opening that may include the features and principles disclosed herein are disclosed in U.S. patent application Ser. No. 16/433,773 filed on Jun. 6, 2019, the disclosure of which is incorporated herein, in its entirety, by this reference.

Figure 6:
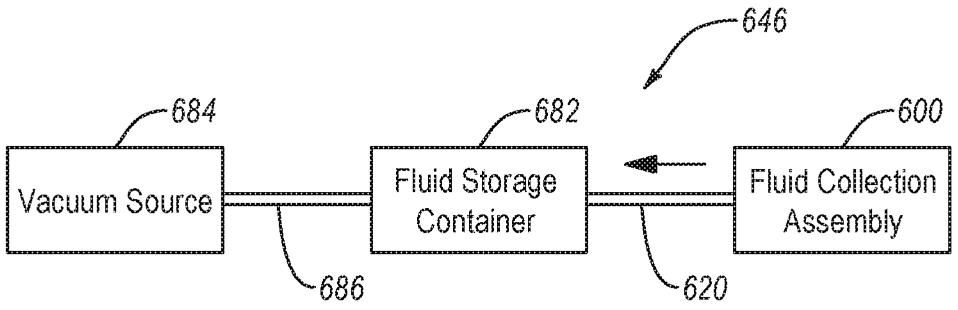
FIG. 6 is a schematic illustration of fluid collection system that includes a fluid collection assembly, according to an embodiment.

FIG. 6 is a schematic illustration of fluid collection system 680 that includes a fluid collection assembly 600, according to an embodiment. The fluid collection assembly 600 may include any of the fluid collection assemblies disclosed herein. The fluid collection assembly 600 may be in fluid communication with a fluid storage container 646 via, for example, at least one first tube 620 (e.g., tube 120 of FIGS. 1A and 1B). The fluid storage container 646 is positioned downstream from the fluid collection assembly 600. The fluid storage container 646 may be in fluid communication with a vacuum source 684 via at least one second tube 686. The vacuum source 684 is positioned downstream from the fluid storage container 646. During operation, the vacuum source 684 provides a suction force to the fluid collection assembly 600. The suction force draws fluid into the chamber of the fluid collection assembly 600 and towards the first tube 620. The fluid that enters the first tube 620 is pulled by the suction force towards the fluid storage container 646 such that the fluid storage container 646 receives the bodily fluids. The fluid storage container 646 may be configured to inhibit the fluid from flowing from the fluid storage container 646 to the vacuum source 684.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean ±10%, ±5%, +2% or 0% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

What is claimed is:

1. A fluid collection assembly, comprising:

a fluid impermeable barrier including a first end region and a second end region longitudinally spaced from the first end region, the fluid impermeable barrier including a sump that forms at least a portion of the first end region, the sump defining a hole, the fluid impermeable barrier defining:

at least one opening;

a chamber in fluid communication with the at least one opening;

a fluid reservoir defined by at least a portion of the sump; and a fluid outlet in fluid communication with the fluid reservoir, wherein the hole is distinct from the fluid outlet;

at least one wicking material disposed in the chamber; and a sample port directly attached to portions of the sump about the hole, the sample port in fluid communication with the fluid reservoir, the sample port configured to switch between a closed state that restricts fluid flow through the sample port and an open state that permits fluid flow through the sample port, the sample port configured to be connected to a fluid collector.

2. The fluid collection assembly of claim 1, wherein the at least a portion the sump exhibits a rigidity that is greater than the rest of the fluid impermeable barrier.

3. The fluid collection assembly of claim 2, further comprising a support structure supporting and providing rigidity to the at least a portion of the sump.

4. The fluid collection assembly of claim 1, wherein one or more regions of the sump are at least partially transparent.

5. The fluid collection assembly of claim 1, wherein the sump is integrally formed with the rest of the fluid impermeable barrier.

6. The fluid collection assembly of claim 1, wherein the sump is distinct from the rest of the fluid impermeable barrier.

7. The fluid collection assembly of claim 1, wherein the fluid reservoir is substantially unoccupied and the fluid reservoir exhibits a length that is greater than about 2.5 cm, wherein the length of the fluid reservoir is measured parallel to a longitudinal axis of the fluid impermeable barrier.

8. The fluid collection assembly of claim 1, wherein the fluid reservoir exhibits a maximum reservoir width that is greater than a maximum chamber width of the chamber, wherein the maximum reservoir width is measured perpendicularly to the longitudinal axis of the fluid impermeable barrier and the maximum chamber width is measured parallel to the maximum reservoir width.

9. The fluid collection assembly of claim 1, wherein the sample port is attached to the first end region of the fluid impermeable barrier.

10. The fluid collection assembly of claim 1, wherein the sample port extends from a back surface of the fluid impermeable barrier, wherein the back surface of the fluid impermeable barrier is opposite the at least one opening.

11. The fluid collection assembly of claim 1, wherein the sample port is a split septum fitting.

12. The fluid collection assembly of claim 1, wherein the sample port forms part of a luer-lock mechanism.

13. The fluid collection assembly of claim 1, wherein the sample port is at least one of ultrasonically welded or heat staked to the fluid impermeable barrier.

14. The fluid collection assembly of claim 1, wherein the sample port includes a tube.

15. The fluid collection assembly of claim 1, wherein the sample port is configured to be in the closed state when the sample port is not attached to the fluid collection and in the open state when the fluid collector is attached to the sample port.

16. A fluid collection system, comprising:
- a fluid collection assembly of including:
- a fluid impermeable barrier including a first end region and a second end region longitudinally spaced from the first end region, the fluid impermeable barrier including a sump that forms at least a portion of the first end region, the sump defining a hole, the fluid impermeable barrier defining:
  - at least one opening;
  - a chamber in fluid communication with the at least one opening;
  - a fluid reservoir defined by at least a portion of the sump; and
  - a fluid outlet in fluid communication with the fluid reservoir, wherein the hole is distinct from the fluid outlet;
- at least one wicking material disposed in the chamber; and
- a sample port directly attached to portions of the sump about the hole, the sample port in fluid communication with the fluid reservoir, the sample port configured to switch between a closed state that restricts fluid flow through the sample port and an open state that permits fluid flow through the sample port, the sample port configured to be connected to a fluid collector;
- the fluid collector configured to be connected to the sample port.

17. The fluid collection system of claim 16, wherein the fluid collector includes a needleless syringe.

18. The fluid collection system of claim 16, wherein the fluid collector includes a vial.

19. A method of using a fluid collection system, the method comprising:
- attaching a fluid collector to a sample port of a fluid collection assembly, the fluid collection assembly including a first end region and a second end region longitudinally spaced from the first end region, a fluid impermeable barrier including a sump that forms at least a portion of the first end region, the sump defining a hole, the sample port directly attached to portions of the sump about the hole, the sample port configured to switch between a closed state that restricts fluid flow through the sample port and an open state that permits fluid flow through the sample port, the fluid impermeable barrier defining at least one opening, a chamber in fluid communication with the at least one opening, a fluid reservoir defined by at least a portion of the sump, and a fluid outlet in fluid communication with the fluid reservoir, wherein the hole is distinct from the fluid outlet;
- receiving bodily fluids from an individual through the at least one opening, into a chamber that includes at least one wicking material disposed therein, and to a fluid reservoir;
- when the sample port is in the open state, removing at least some of the bodily fluids that are present in the fluid reservoir with the fluid collector;
- detaching the fluid collector from the sample port;
- switching the sample port from the open state to the closed state; and
- removing substantially all of a remainder of the bodily fluids present in the fluid reservoir through the fluid outlet using a suction force.

20. The method of claim 19, wherein attaching the fluid collector to the sample port includes switching the sample port from the closed state to the open state thereof.

21. The method of claim 19, wherein detaching the fluid collector from the sample port and switching the sample port from the open state to the closed state are performed simultaneously.

22. The method of claim 19, further comprising, before removing at least some of the bodily fluids that are present in the fluid reservoir with the fluid collector, stopping applying the suction force to the chamber.

* * * * *